United States Patent [19]

Itoh et al.

[11] Patent Number: 4,612,329

[45] Date of Patent: Sep. 16, 1986

[54] PHARMACEUTICAL ALPHA-AMINOALKYL-ALPHA-ALKYL-PHENYLACETONITRILES

[75] Inventors: Yasuo Itoh; Hideo Kato; Eiichi Koshinaka; Nobuo Ogawa; Sakae Kurata; Hiroyuki Nishino; Toshihiko Yoshida, all of Fukui, Japan

[73] Assignee: Hokuriku Pharmaceutical Co., Ltd., Katsuyamashi Fukui, Japan

[21] Appl. No.: 786,742

[22] Filed: Oct. 11, 1985

[30] Foreign Application Priority Data

Oct. 17, 1984 [JP] Japan .................................. 59-216399
Jul. 22, 1985 [JP] Japan .................................. 60-160278

[51] Int. Cl.$^4$ .................. A61K 31/275; C07C 121/78
[52] U.S. Cl. .................................. 514/523; 514/331; 546/230; 558/408; 558/409
[58] Field of Search ................. 260/465 E; 546/230; 514/523, 331

[56] References Cited

U.S. PATENT DOCUMENTS 3,261,859  7/1966  Dengel ..................... 260/465 E
4,438,131  3/1984  Ehrmann et al. ............... 514/523

Primary Examiner—Dolph H. Torrence
Attorney, Agent, or Firm—Gordon W. Hueschen

[57] ABSTRACT

Novel alpha-aminoalkyl-alpha-alkylphenylacetonitrile derivatives useful for treatment of cartino vaso diseases, a peripheral circulatory insufficiency and cerebral circulation failure are disclosed.

13 Claims, No Drawings

PHARMACEUTICAL ALPHA-AMINOALKYL-ALPHA-ALKYL-PHENYLACETONITRILES

BACKGROUND OF THE INVENTION

1. Field of the Invention

The present invention relates to novel alpha-aminoalkylalpha-alkylphenylacetonitrile derivatives and pharmaceutically acceptable acid addition salts thereof which exhibit an effective cerebral vascular dilator activity, calcium antagonistic activity and an excellent anti-arrhythmic activity and alpha-blocking activity and can be used for treatment of cartino vaso diseases, a peripheral circulatory insufficiency and cerebral circulation failure, to process for the preparation thereof, pharmaceutical compositions thereof and method of treating therewith.

2. Description of the Prior Art

It is already known that Verapamil (general name, Merck Index, 10th Edition, 9748) represented by formula (II):

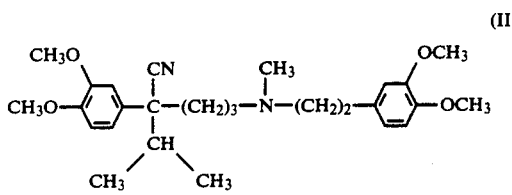

and Gallopamil (general name, USAN and USP Dictionary of Drug Names, 1985, Page 232), which is a derivative of Verapamil, and is represented by formula (III):

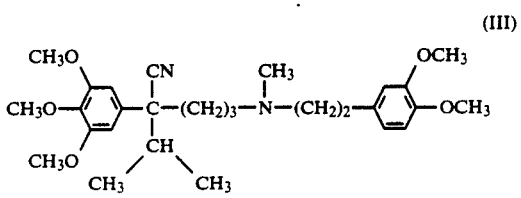

have effective calcium antagonistic action and are therapeutically useful as a vasodilator(coronary) and cardiac depressant (anti-arrhythmic) and especially the former has been already marketed widely for clinical use.

Furthermore, it is also known that Disopyramide (general name, Merck Index, 10th Edition, 3378) represented by formula:

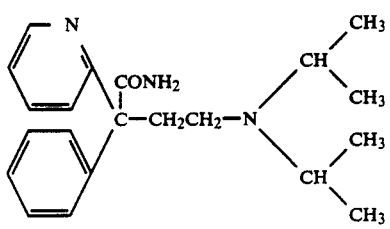

has excellent anti-arrhythmic activity and alpha blocking action.

SUMMARY OF THE INVENTION

As a result of extensive investigations, it has been found that novel alpha-aminoalkyl-alpha-alkyl-phenylacetonitrile derivatives represented by the general formula (I)

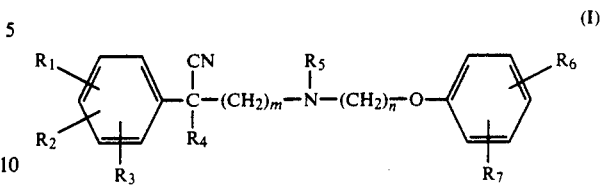

wherein $R_1$, $R_2$ and $R_3$, which may be the same or different, each represents hydrogen or lower alkoxy, $R_4$ represents a straight- or branched-chain lower alkyl, $R_5$ represents hydrogen or lower alkyl, $R_6$ and $R_7$, which may be the same or different, each represents hydrogen, halogen, lower alkyl, halogeno lower alkyl, lower alkoxy, nitro, amino, hydroxyalkyl, benzyloxy, cyano or piperidinomethyl and m and n are an integral of 2 or 3 and the pharmaceutically-acceptable acid addition salts thereof, exhibit more excellent calcium antagonistic activity compared with Verapamil and more excellent anti-arrhythmic activity and alpha-blocking activity than Disopyramide.

Further, according to the present invention, there are provided the process for preparation of the novel alpha-aminoalkyl-alpha-alkylphenylacetonitrile derivatives represented by the general formula (I), as well as pharmaceutical compositions thereof and method of treating therewith.

DETAILED DESCRIPTION OF THE INVENTION

In this invention, by the term "lower" in formula (I) is meant a straight or branched carbon chain having 1–5 carbon atoms. Therefore, the lower alkoxy moiety represented by $R_1$, $R_2$, $R_3$, $R_6$, and $R_7$ in the formula (I) includes, for example, methoxy, ethoxy, propoxy, butoxy, pentoxy and the like. The lower alkyl moiety as represented by $R_4$, $R_5$, $R_6$, and $R_7$ in the general formula (I) includes, for example, methyl, ethyl, propyl, isopropyl, butyl, iso-butyl, sec-butyl, tert-butyl, pentyl, and the like. As halogen represented by $R_6$ and $R_7$ can be used: fluorine, chlorine, bromine, iodine. As halogeno lower alkyl can be used, for example: fluoromethyl, difluoromethyl, trifluoromethyl, 2-fluoroethyl, 2-trifluoroethyl, and the like. As hydroxyalkyl can be used for example: hydroxymethyl, hydroxyethyl and the like.

Pharmaceutically-acceptable acid addition salts of the compound represented by the formula (I) include, for example, mineral salts such as hydrochloride, hydrobromide, hydroiodide, nitrate, sulfate, phosphate, and the like.; or organic acid salts such as acetate, maleate, fumarate, citrate, oxalate, malate, tartarate, and the like.

According to the present invention the novel compounds, novel alpha-aminoalkyl-alpha-alkyl-phenylacetonitrile derivatives represented by the formula (I), can be prepared by various methods.

In the first method, the compound represented by the said formula (I) is prepared by reacting an aldehyde derivative represented by the general formula (V),

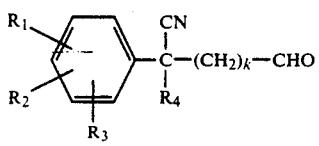

(V)

wherein $R_1$, $R_2$, $R_3$ and $R_4$, each has the same meaning as that described above, while k is 1 or 2, with an amine derivative represented by the formula (VI):

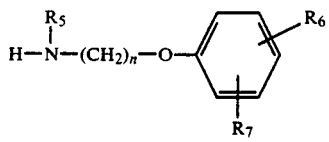

(VI)

wherein $R_5$, $R_6$, $R_7$, and n have the same meaning as that described above in the presence of a solvent and treating with a reducing agent.

The solvent used in the process can be any kind so long as it does not inhibit the reaction, for example, methanol, ethanol, butanol, ether, tetrahydrofuran, or the like.

As reducing agent in the present reaction can be used, for example, sodium borohydride, lithium aluminium hydride, or the like.

The above-mentioned reaction is to be carried out within the temperature range from room temperature to the reflux temperature of the reaction solvent used.

In the second method, the inventive compound represented by the formula (I) is prepared by alkylation of the nitrogen of a phenylacetonitrile derivative represented by the formula (VII)

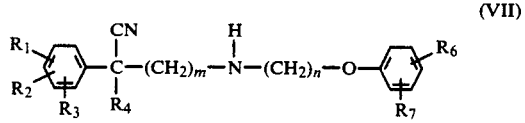

(VII)

wherein $R_1$, $R_2$, $R_3$, $R_4$, $R_6$, $R_7$, m, and n have the same meaning as that described above and which corresponds to a compound of the formula (I), wherein $R_5$ means hydrogen.

As agent for alkylation in the present invention is used an alkyl halogenide represented by the formula (IX):

$$R_5-X \quad \text{(VIII)}$$

wherein $R_5$ has the same meaning as that described above and X represents halogen or a carbonyl compound represented by formula (IX):

(IX)

wherein $R_8$ represents hydrogen or lower alkyl.

As carbonyl compound represented by the formula (IX) in the present invention can be used formaldehyde, acetaldehyde, propionaldehyde, or the like. Formaldehyde is used preferably in the form of its aqueous solution (formaline). In the case of acetaldehyde or propionaldehyde, it is preferable to use nitrobenzene as a solvent for the reaction.

The carbonyl compound in the present invention is to be used preferably in the presence of formic acid or sodium borohydride and the reaction is to be conducted at a temperature within the range of 100° and 200° C. and preferably at the reflux temperature of the reaction solvent.

In the third method of this invention, an inventive compound represented by the formula (X):

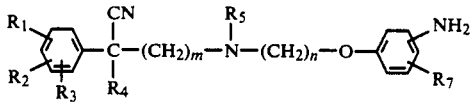

(X)

wherein $R_1$, $R_2$, $R_3$, $R_4$, $R_5$, $R_7$, m, and n have the same meaning as that described above and which corresponds to a compound represented by formula (I), in which $R_6$ means an amino group is prepared by treating a compound represented by formula (XI):

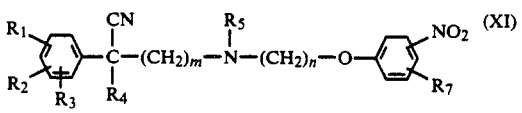

(XI)

wherein $R_1$, $R_2$, $R_3$, $R_4$, $R_5$, $R_7$, m, and n have the same meaning as that described above and which corresponds to a compound represented by formula (I), wherein $R_6$ means a nitro group, with a reducing agent or by hydrogenation in the presence of metallic catalyzer.

As reducing agent in the present invention is used, for example, a metal or metallic salt such as iron and tin, or as metallic catalyzer, for example, such as Raney nickel, platinum, palladium, copper, or the like. The solvent used in the process is, for example, water, hydrochloric acid, acetic acid, or an alcohol such as methanol, ethanol, or the like.

The reaction is performed at a temperature between room temperature and the reflux temperature of the solvent used.

The invention also includes a pharmaceutical composition for use in the treatment of cartino vaso diseases, peripheral circulatory insufficiency and cerebral circulation failure, comprising an effective amount of one or more compounds of the invention, together, with a compatible, pharmaceutical by-acceptable carrer or coating.

Typical examples of alpha-aminoalkyl-alpha-alkyl-phenyl acetonitrile compounds embraced by the present invention are:

Alpha-isopropyl-alpha-[2-[N-[3-(2-methoxyphenoxy)-propyl]amino]ethyl]-3,4,5-trimethoxyphenylacetonitrile Alpha-isopropyl-alpha-[3-[N-[2-(3-methylphenoxy)ethyl]-N-methylamino]propyl]-3,4,5-trimethoxyphenylacetonitrile Alpha-isopropyl-alpha-[3-[N-[2-(2-methoxyphenoxy)ethyl]amino]propyl]-3,4,5-trimethoxyphenylacetonitrile Alpha-ethyl-alpha-[3-[N-[2-(2-methoxyphenoxy)ethyl]amino]propyl]-3,4,5-trimethoxyphenylacetonitrile Alpha-isobutyl-alpha-[3-[N-[2-(2-methoxyphenoxy)ethyl]amino]propyl]-3,4,5-trimethoxyphenylacetonitrile Alpha-isopropyl-alpha-[3-[N-[3-(3-methylphenoxy)propyl]-N-methylamino]propyl]-3,4,5-trimethoxyphenylacetonitrile Alpha-isopropyl-alpha-[3-[N-[3-(3-methoxyphenoxy)propyl]-N-methylamino]propyl]-3,4,5-trimethoxyphenylacetonitrile Alpha-isopropyl-alpha-[3-[N-[3-(2-methoxyphenoxy)propyl]amino]propyl]-3,4,5-trimethoxyphenylacetonitrile Alpha-ethyl-alpha-[3-[N-[3-(3-methoxyphenoxy)propyl]-N-methylamino]propyl]-3,4,5-trimethoxyphenylacetonitrile Alpha-propyl-alpha-[3-[N-[3-(3-methoxyphenoxy)propyl]-N-methylamino]propyl]-3,4,5-trimethoxyphenylacetonitrile Such prepared alpha-aminoalkyl-alpha-alkyl-phenylacetonitrile represented by the formula (I) and the pharmaceutically-acceptable acid addition salts thereof exhibit an effective calcium antagonistic activity, an excellent antiarrhythmic activity, and alpha-blocking activity, and can be used for treatment of cartino vaso diseases, a peripheral circulatory insufficiency, and cerebral circulation failure.

Calcium antagonistic activity is shown in Table 1, antiarrhythmic activity and alpha-blocking activity are shown in Tables 2 and 3, respectively, as one example representing the effective activity of the present compounds, while using Verapamil, Gallopamil and Disopyramide as reference drug.

1. $Ca^{2+}$ antagonistic action

The taenia coil was excised from male Hartley guinea-pig and mounted in a tissue bath containing $Ca^{2+}$-free 100 mM KCl LockeRinger solution. A resting tension of 0.5 g was applied to the tissue. The contraction, which was induced by cumulative application of $CaCl_2$, was measured by the isotonic transducer. The tissue bath solution was maintained at 37° C. and bubbled with a mixture of 95% $O_2$–5% $CO_2$. The test compounds were applied 30 min prior to cumulative application of $CaCl_2$. The degree of $Ca^{2+}$ antagonistic action was expressed as the $pA_2$ value. The $pA_2$ values were calculated from dose-ratios which were obtained as the ratio of the concentrations of $CaCl_2$ producing a 50% maximal response in the presence and absence of the test compound.

TABLE 1

| $Ca^{2+}$ antagonistic action | |
|---|---|
| Test Compound | $pA_2$ value |
| Example 13 | 8.11 |
| Example 14 | 8.15 |
| Example 80 | 8.52 |
| Example 95 | 8.19 |
| Example 97 | 8.02 |
| Example 99 | 8.29 |
| Example 105 | 8.14 |
| Example 111 | 8.48 |
| Example 113 | 8.31 |
| Example 117 | 8.81 |
| Example 119 | 8.05 |
| Example 129 | 8.13 |
| Example 133 | 8.17 |
| Example 163 | 8.17 |
| Example 165 | 8.03 |
| Example 169 | 8.85 |
| Example 175 | 8.56 |
| Example 179 | 8.36 |
| Example 183 | 8.30 |

TABLE 1-continued

| $Ca^{2+}$ antagonistic action | |
|---|---|
| Test Compound | $pA_2$ value |
| Verapamil | 7.59 |
| Gallopamil | 8.56 |

2. Anti-arrhythmic action (aconitine-induced arrhythmias in mice)

Male ddY mice weighing about 30 g were anesthetized with pentobarbital sodium given intraperitoneally. Aconitine (1.32 μg/min) was continuously infused into a tail vein 15 min posterior to pentobarbital sodium administration. The standard limb lead II electrocardiogram was monitored by the cathode ray oscilloscope and the appearance of premature ventricular systoles was observed. The amount of aconitine needed to induce arrhythmias was calculated from the time taken to the onset of the first premature ventricular systoles. The test compounds (100 mg/kg) were orally given 60 min prior to aconitine infusion. Their relative potencies to quinidine were compared by the percent increase of aconitine needed to induce arrhythmias.

TABLE 2

| Anti-arrhythmic action | |
|---|---|
| Test Compound | relative potency (quinidine = 1) |
| Example 3 | 2.01 |
| Example 6 | 2.02 |
| Example 11 | 1.51 |
| Example 19 | 2.28 |
| Example 20 | 1.20 |
| Example 25 | 2.34 |
| Example 26 | 1.60 |
| Example 27 | 1.43 |
| Example 57 | 1.52 |
| Example 58 | 1.64 |
| Example 84 | 2.52 |
| Example 85 | 3.72 |
| Example 88 | 1.34 |
| Example 118 | 2.65 |
| Example 119 | 2.24 |
| Example 122 | 1.21 |
| Example 126 | 1.03 |
| Example 128 | 2.01 |
| disopyramide | 0.97 |
| Verapamil | −0.02 |
| Gallopamil | 0.30 |

3. Alpha-receptor blocking action

The thoracic aorta was excised from male rabbit and helically cut. The helical strip was mounted in a tissue bath containing Krebs-Henseleit solution maintained at 37° C. A resting tension of 2.0 g was applied to the tissue. The change in tension, which was induced by cumulative application of noradrenaline, was isometrically measured by the FD-pickup. The tissue bath solution was bubbled with a mixture of 95% $O_2$–5% $CO_2$. The test compounds were applied 30 min prior to cumulative application of noradrenaline. The degree of alpha-blocking action was expressed as the $pA_2$ value. The $pA_2$ values were calculated from dose-ratios which were obtained as the ratio of the concentrations of noradrenaline producing a 50% maximal response in the presence and absence of the test compound.

TABLE 3

| Alpha-blocking action | |
|---|---|
| Test Compound | $pA_2$ value |
| Example 4 | 8.25 |
| Example 21 | 8.02 |

TABLE 3-continued

| Alpha-blocking action | |
|---|---|
| Test Compound | pA$_2$ value |
| Example 84 | 8.42 |
| Example 88 | 8.40 |
| Example 90 | 8.79 |
| Example 91 | 8.46 |
| Example 92 | 8.57 |
| Example 93 | 8.67 |
| Verapamil | 6.41 |
| Gallopamil | 6.11 |

A compound of the present invention represented by general formula (I) can be administered per os, e.g., in the form of pills or tablets, in which it may be present together with any of the usual pharmaceutical carriers, conventionally by compounding the compound of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terraalba, dicalcium acacia, or the like. Representative liquid carriers are peanut oil, sesame oil, olive oil, water, or the like. The active agents of this invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution.

The invention also includes a method for the treatment of a subject in need of treating cartino vaso diseases, peripheral circulatory insufficiency and cerebral circulation failure, comprising the step of administering to the said subject a sufficient amount for such purpose of a compound of the invention.

The method of using the compounds of this invention comprises internally or externally administering a compound of this invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 1 to about 1000 mg per day (divided into three parts), preferably in 5 to 300 mg per day (divided into three parts) for an oral dose, while parenteral dosages are usually less and ordinarily about one-half of the oral dose. The unit dose is preferably given a suitable number of times daily, typically three times.

The unit dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The present invention is further illustrated by the following Examples but it, is to be understood that the present invention is not limited in terms of the specific process conditions.

REFERENCE

3-Cyano-3-isopropyl-3-(3,4,5-trimethoxyphenyl)propionaldehyde

To a suspension of 4.68 g of sodium amide in 150 ml of dry tetrahydrofuran were added 15.00 g of alpha-isopropyl-3,4,5-trimethoxyphenylacetonitrile with stirring and under cooling and then 11.94 g of chloroacetaldehyde diethyl acetal at room temperature, and the mixture was refluxed for 1.5 hours. After cooling, 40 ml of water was added to the mixture and solvent was evaporated. The residue was dissolved in ether and the solution was washed with water. The ether layer was dried and evaporated to give 21.99 g of alpha-isopropyl-alpha-(beta-diethoxyethyl)-3,4,5-trimethoxyphenylacetonitrile as a colorless oil.

Mass Spectrum m/z: 365 (M+).

A solution of 21.99 g of alpha-isopropyl-alpha-(beta-diethoxyethyl)-3,4,5-trimethoxyphenylacetonitrile in 130 ml of acetone and 66 ml of 10% aqueous oxalic acid was refluxed for 2 hours. After cooling, the solution was adjusted to pH 6 with saturated potassium carbonate solution. The precipitate was filtered off and the filtrate was evaporated. The residue was dissolved in ether and the solution was washed with water. The ether layer was dried and evaporated to give 17.53 g of the desired compound, which was distillated as a pale yellow oil, b.p. 170°-172° C. ( 6 mm Hg).

Mass Spectrum m/z: 291 (M+).

The compounds described in References 2-16 were prepared in the same manner as that described in Reference 1.

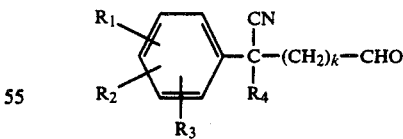

| Reference No. | R$_1$ | R$_2$ | R$_3$ | R$_4$ | k | free base | Mass (M+) |
|---|---|---|---|---|---|---|---|
| 2 | 2-OMe | H | H | iPr | 2 | pale yellow oil | 245 |
| 3 | 3-OMe | H | H | iPr | 2 | brown oil | 245 |
| 4 | 4-OMe | H | H | iPr | 2 | pale yellow oil | 245 |
| 5 | H | H | H | iPr | 2 | pale yellow oil | 215 |
| 6 | 3-OMe | 4-OMe | H | Me | 2 | yellow oil | 247 |
| 7 | 3-OMe | 4-OMe | 5-OMe | Me | 1 | yellowish brown oil | 245 |
| 8 | 3-OMe | 4-OMe | 5-OMe | Et | 1 | brown oil | 277 |
| 9 | 3-OMe | 4-OMe | 5-OMe | nPr | 1 | brown oil | 291 |
| 10 | 3-OMe | 4-OMe | 5-OMe | nBu | 1 | *pale yellow prisms | 305 |

-continued

| Reference No. | $R_1$ | $R_2$ | $R_3$ | $R_4$ | k | free base | Mass (M+) |
| --- | --- | --- | --- | --- | --- | --- | --- |
| 11— | 3-OMe | 4-OMe | 5-OMe | iBu | 1 | brown oil | 305 |
| 12 | 3-OMe | 4-OMe | 5-OMe | Me | 2 | yellowish brown oil | 277 |
| 13 | 3-OMe | 4-OMe | 5-OMe | Et | 2 | brown oil | 291 |
| 14 | 3-OMe | 4-OMe | 5-OMe | nPr | 2 | yellowish brown oil | 305 |
| 15 | 3-OMe | 4-OMe | 5-OMe | nBu | 2 | yellowish brown oil | 319 |
| 16 | 3-OMe | 4-OMe | 5-OMe | iBu | 2 | reddish orange oil | 319 |

*m.p. 93–95° C. (iPr$_2$O)

EXAMPLE 1

Alpha-isopropyl-alpha-[3-[N-[2-(4-methoxyphenoxy)ethyl]amino]-propyl]-3,4-dimethoxyphenylacetonitrile A solution of 3.96 g of 4-cyano-4-isopropyl-4-(3,4-dimethoxyphenyl)butyraldehyde and 2.00 g of 2-(4-methoxyphenoxy)ethylamine in 50 ml of ethanol was refluxed for 1 hour. To the solution was added 0.55 g of sodium borohydride under ice-cooling, and the solution was stirred for 30 minutes at room temperature. The solvent was removed and the residue was dissolved in 10% hydrochloric acid and washed with ether. The aqueous layer was made alkaline with potassium carbonate and extracted with ethyl acetate. The extract was washed with water, dried, and evaporated. The residue was chromatographed on silica gel using chloroform as an eluent to give 2.93 g of the desired compound as a pale yellow oil.

Mass Spectrum m/z: 426 (M+).

The hydrochloride of this compound was obtained in the usual manner.

EXAMPLE 2

Alpha-isopropyl-alpha-[2-(2-phenoxyethylamino)ethyl]-3,4,5-trimethoxyphenylacetontrile A solution of 6.00 g of 3-cyano-3-isopropyl-3-(3,4,5-trimethoxyphenyl)propionaldehyde and 2.26 g of 3-phenoxypropylamine in 50 ml of methanol was refluxed for 1 hour. To the solution was added 0.76 g of sodium borohydride under ice-cooling and the solution was stirred for 1 hour at room temperature. The solvent was removed and the residue was dissolved in 10% hydrochloric acid and washed with ether. The aqueous layer was mde alkaline with potassium carbonate and extracted with chloroform. The extract was washed with water, dried, and evaporated to give 5.40 g of the desired compound as a pale yellow oil.

Mass Spectrum m/z: 412 (M+).

The hydrochloride of this compound was obtained in the usual manner.

EXAMPLE 3

Alpha-isopropyl-alpha-[3-(2-phenoxyethylamino)-propyl]-3,4,5-trimethoxyphenylacetonitrile Hydrochloride A solution of 3.05 g of 4-cyano-4-isopropyl-4-(3,4,5-trimethoxyphenyl)butyraldehyde and 1.37 g of 2-phenoxyethylamine in 40 ml of ethanol was refluxed for 1 hour. To the solution was added 0.38 g of sodium borohydride under ice-cooling and the solution was stirred for 30 minutes at room temperature. The solvent was removed and to the residue were added 10% hydrochloric acid and ether. The precipitate was filtered and washed with ether to give 2.75 g of the desired compound as colorless crystals.

The free base of this compound was obtained in the usual manner.

Mass Spectrum m/z: 426 (M+).

The compounds described in Examples 4–6 were prepared in the same manner as that described in Examples 1–3.

EXAMPLE 4

Alpha-isopropyl-alpha-[3-[N-[2-(2-methoxyphenoxy)ethyl]amino]-propyl]-3,4-dimethoxyphenylacetonitrile Maleate

EXAMPLE 5

Alpha-isopropyl-alpha-[3-[N-[2-(2-methylphenoxy)ethyl]amino]-propyl]-3,4-dimethoxyphenylacetonitrile Hydrochloride

EXAMPLE 6

Alpha-isopropyl-alpha-[2-[N-[3-(2-methoxyphenoxy)propyl]-amino]ethyl]-3,4,5-trimethoxyphenylacetonitrile Hydrochloride

EXAMPLE 7

Alpha-isopropyl-alpha-[3-[N-[2-(2-methoxyphenoxy)ethyl]-N-methylamino]propyl]-3,4-dimethoxyphenylacetonitrile A mixture of 2.35 g of alpha-isopropyl-alpha-[3-[N-[2-(2-methoxyphenoxy)ethyl]amino]propyl]-3,4-dimethoxyphenylacetonitrile, 8 ml of 37% formalin, and 16 ml of 90% formic acid was stirred for 1 hour at 110° C. After cooling, to the mixture were added water and potassium carbonate to make it alkaline. The solution was extracted with chloroform and the extract was washed with water, dried, and evaporated. The residue was chromatographed on silica gel using chloroform as an eluent to give 1.30 g of the desired compound as a pale yellow oil.

EXAMPLE 8

Alpha-isopropyl-alpha-[3-[N-[2-(2-methylphenoxy)ethyl]-N-methylamino]propyl]-3,4-dimethoxyphenylacetonitrile 1.84 g of alpha-isopropyl-alpha-[3-[N-[2-(2-methoxyphenoxy)ethyl]amino]propyl]-3,4-dimethoxyphenylacetonitrile hydrochloride, 5.5 ml of 37% formalin, and 11 ml of 90% formic acid were treated in the same manner as that described in Example 7 to give 1.14 g of the desired compound as a colorless oil.

EXAMPLE 9

Alpha-isopropyl-alpha-[2-[N-[3-(2-methoxyphenoxy)propyl]-N-methylamino]ethyl]-3,4,5-trimethoxyphenylacetonitrile A mixture of 0.39 g of alpha-isopropyl-alpha-[2-[N-[3-(2-methoxyphenoxy)propyl]amino]ethyl]-3,4,5-trimethoxyphenylacetonitrile, 1 ml of 37% formalin, and 1 ml of 90% formic acid was refluxed for 1 hour.

After cooling, to the mixture were added water and potassium carbonate to make it alkaline. The solution was extracted with chloroform. The extract was washed with water, dried, and evaporated to give 0.23 g of desired compound as a yellow oil.

EXAMPLE 10

Alpha-isopropyl-alpha-[3-[N-[3-(2-nitrophenoxy)-propyl]amino]-propyl]-3,4,5-trimethoxyphenylacetonitrile A solution of 8.09 g of 4-cyano-4-isopropyl-4-(3,4,5-trimethoxyphenyl)butyraldehyde and 4.96 g of 3-(2-nitrophenoxy)-propylamine in 100 ml of methanol was refluxed for 3 hours. After cooling, to the solution was added 0.50 g of sodium borohydride and the solution was stirred overnight at room temperature. The solvent was removed and to the residue was added water. The solution was extracted with chloroform and the extract was washed with water, dried, and evaporated. The residue was chromatographed on silica gel using 10% methanol-chloroform as an eluent to give 6.48 g of the desired compound as a pale yellow oil.

The oxalate of this compound was obtained in the usual manner.

EXAMPLE 11

Alpha-isopropyl-alpha-[3-[N-[3-(2-aminophenoxy)-propyl]amino]-propyl]-3,4,5-trimethoxyphenylacetonitrile 4.78 g of alpha-isopropyl-alpha-[3-[N-[3-(2-nitrophenoxy)propyl]amino]propyl]-3,4,5-trimethoxyphenyl-acetonitrile was hydrogenated in 100 ml of methanol over 50 mg of platinum oxide at atmospheric pressure and room temperature. The catalyst was filtered off and filtrate was evaporated to give 4.36 g of desired compound as a pale yellow oil.

The oxalate of this compound was obtained in the usual manner.

EXAMPLE 12

Alpha-isopropyl-alpha-[3-[N-[3-(2-nitrophenoxy)-propyl]-N-methylamino]propyl]-3,4,5-trimethoxy-phenylacetonitrile A mixture of 2.58 g of alpha-isopropyl-alpha-[3-[N-[3-(2-nitrophenoxy)propyl]amino]propyl]-3,4,5-trimethoxyphenylacetonitrile, 4.35 ml of 37% of formalin, and 4.35 ml of 90% formic acid was stirred for 1 hour at 90° C. After cooling, to the mixture were added water and potassium carbonate to make it alkaline. The solution was extracted with chloroform and the extract was washed with water, dried, and evaporated. The residue was chromatographed on silica gel using 1% methanol-chloroform as an eluent to give 1.43 g of the desired compound as a yellow oil.

EXAMPLE 13

Alpha-isopropyl-alpha-[3-[N-[3-(3-hydroxymethyl-phenoxy)propyl]-N-methylamino]propyl]-3,4,5-trimethoxyphenylacetonitrile A solution of 2.80 g of alpha-isopropyl-alpha-[3-[N-[3-(3-hydroxymethylphenoxy)propyl]amino]propyl]-3,4,5-trimethoxyphenyl acetonitrile and 4.84 g of 37% formalin in 70 ml of methanol was refluxed for 1 hour. After cooling, to the solution was added 2.25 g of sodium borohydride and the solution was stirred for 1 hour at room temperature. The solvent was removed and to the residue was added water. The solution was extracted with chloroform and the extract was washed with water, dried, and evaporated. The residue was chromatographed on silica gel using 10% methanol-chloroform as an eluent to give 0.74 g of the desired compound as a yellow oil.

EXAMPLE 14

Alpha-isopropyl-alpha-[3-[N-[3-(2-aminophenoxy)-propyl]-N-methylamino]propyl]-3,4,5-trimethoxy-phenylacetonitrile 0.92 g of alpha-isopropyl-alpha-[3-[N-[3-(2-nitrophenoxy)propyl]-N-methylamino]propyl]-3,4,5-trimethoxyphenylacetonitrile was hydrogenated in 20 ml of methanol over 10 mg of platinum oxide at atmospheric pressure and room temperature. The catalyst was filtered off and filtrate was evaporated to give 0.91 g of the desired compound as a yellow oil. The oxalate of this compound was obtained in the usual manner.

The compounds obtained in Examples 15–185 were prepared in the same manner as described in Examples 1–14.

The physical and chemical properties of the compounds in Examples 1–185 are shown in Table 4 and 5.

TABLE 4 structure:
$$\underset{R_2}{\underset{R_1}{\text{Ar}}}\text{—C(CN)(R}_4\text{)—(CH}_2)_m\text{—N(R}_5)\text{—(CH}_2)_n\text{—O—Ar'(R}_6,R_7)$$

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 1 | 3-OMe | 4-OMe | H | 3 | 2 | iPr | H | 4-OMe | H | free base, pale yellow oil | 426 | 2230 (liq) | 0.80,1.19(each 3H,d,J=6.5Hz),3.76(3H,s),3.87(6H,s),3.98(2H,t,J=5.5Hz) [in CDCl₃] |
| 2 | 3-OMe | 4-OMe | 5-OMe | 2 | 2 | iPr | H | H | H | free base, pale yellow oil | 412 | 2230 (liq) | 0.86,0.98(each 3H,d,J=6.5Hz),3.79,3.81(9H,each s),4.16(2H,t,J=5.0Hz),7.25(5H,s),6.68(2H,s) [in CDCl₃] |
| 3 | 3-OMe | 4-OMe | 5-OMe | 3 | 2 | iPr | H | H | H | free base, pale yellow oil | 426 | 2230 (liq) | 0.82,1.21(each 3H,d,J=6.5Hz),3.85(9H,s),3.99(2H,t,J=5.5Hz),6.58(2H,s) [in CDCl₃] |
| 4 | 3-OMe | 4-OMe | H | 3 | 2 | iPr | H | 2-OMe | H | free base, pale yellow oil | 427 (M⁺+1) | 2230 (liq) | 0.80,1.19(each 3H,d,J=6.5Hz),3.83(3H,s),3.87(6H,s),4.05(2H,t,J=5.5Hz) [in CDCl₃] |
| 5 | 3-OMe | 4-OMe | H | 3 | 2 | iPr | H | 2-Me | H | free base, pale yellow oil | 410 | 2240 (liq) | 0.80,1.19(each 3H,d,J=6.5Hz),2.20(3H,s),3.87(6H,s),4.02(2H,t,J=5.5Hz) [in CDCl₃] |
| 6 | 3-OMe | 4-OMe | 5-OMe | 2 | 2 | iPr | H | 2-OMe | H | free base, hydrochloride | 456 | 2240 (KBr) | 0.81,1.26(each 3H,d,J=6.5Hz),3.77(3H,s),3.85(3H,s),3.87(6H,s),4.12(2H,t,J=5.5Hz),6.75(2H,s) [in CD₃OD] |
| 7 | 3-OMe | 4-OMe | H | 3 | 2 | iPr | Me | 2-OMe | H | free base, pale yellow oil | 440 | 2230 (liq) | 0.79,1.18(each 3H,d,J=6.5Hz),2.23(3H,s),3.84(3H,s),3.87(6H,s),4.07(2H,t,J=6.0Hz) [in CDCl₃] |
| 8 | 3-OMe | 4-OMe | 5-OMe | 3 | 2 | iPr | Me | 2-Me | H | free base, colorless oil | 424 | 2230 (liq) | 0.79,1.18(each 3H,d,J=6.5Hz),2.20(3H,s),2.24(3H,s),3.87(6H,s),4.02(2H,t,J=5.5Hz) [in CDCl₃] |
| 9 | 3-OMe | 4-OMe | 5-OMe | 3 | 2 | iPr | Me | 2-OMe | H | free base, yellow oil | 470 | 2230 (liq) | 0.79,1.17(each 3H,d,J=6.5Hz),2.21(3H,s),3.82(3H,s),3.85(9H,s),4.02(2H,t,J=6.5Hz),6.57(2H,s),6.89(4H,s) [in CDCl₃] |
| 10 | 3-OMe | 4-OMe | 5-OMe | 3 | 3 | iPr | H | 2-OMe | H | oxalate | 485 | 2210 (KBr) | 0.78,1.22(each 3H,d,J=6.5Hz),3.74(3H,s),3.85(6H,s),4.25(2H,t,J=5.5Hz),6.72(2H,s) [in CD₃OD] |
| 11 | 3-OMe | 4-OMe | 5-OMe | 3 | 3 | iPr | H | 2-NO₂ | H | oxalate | 455 | 2210 (KBr) | 0.71,1.13(each 3H,d,J=6.0Hz),3.67(3H,s),3.80(6H,s),3.96(2H,t,J=6.0Hz),6.67(2H,s) [in DMSO-d₆] |
| 12 | 3-OMe | 4-OMe | 5-OMe | 3 | 3 | iPr | Me | 2-NO₂ | H | free base, yellow oil | 499 | 2250 (liq) | 0.79,1.17(each 3H,d,J=7.0Hz),2.13(3H,s),3.85(3H,s),3.86(6H,s),4.14(2H,t,J=6.0Hz),6.15(2H,s) [in CDCl₃] |
| 13 | 3-OMe | 4-OMe | 5-OMe | 3 | 3 | iPr | Me | 3-CH₂OH | H | free base | 434 | 2240 (liq) | 0.80,1.15(each 3H,d,J=6.5Hz),2.12(3H,s),3.84(9H,s),3.98(2H,t,J=6.5Hz),4.63(2H,s),6.58(2H,s) [in CDCl₃] |
| 14 | 3-OMe | 4-OMe | 5-OMe | 3 | 3 | iPr | Me | 2-NH₂ | H | oxalate | 469 | 2240 (KBr) | 0.79,1.21(each 3H,d,J=7.0Hz),2.80(3H,s),3.76(3H,s),3.85(6H,s),4.11(2H,t,J=6.0Hz),6.72(2H,s) [in DMSO-d₆] |
| 15 | H | H | H | 3 | 2 | iPr | H | 2-OMe | H | free base, colorless oil | 366 | 2240 (liq) | 0.78,1.20(each 3H,d,J=6.5Hz),3.83(3H,s),4.07(2H,t,J=5.5Hz),6.89(4H,s),7.35(5H,s) [in CDCl₃] |
| 16 | H | H | H | 3 | 2 | iPr | Me | 2-OMe | H | free base, pale orange oil | 380 | 2230 (liq) | 0.77,1.18(each 3H,d,J=6.5Hz),2.21(3H,s),3.84(3H,s),4.05(2H,t,J=6.0Hz),6.89(4H,s),7.36(5H,s) [in CDCl₃] |
| 17 | H | H | H | 3 | 3 | iPr | H | 2-OMe | H | free base, colorless oil | 380 | 2240 (liq) | 0.77,1.18(each 3H,d,J=6.5Hz),3.79(3H,s),4.07(2H,t,J=6.0Hz),6.88(4H,s) [in CDCl₃] |
| 18 | H | H | H | 3 | 2 | iPr | Me | 2-OMe | H | free base, colorless oil | 394 | 2240 (liq) | 0.76,1.17(each 3H,d,J=6.5Hz),2.09(3H,s),3.85(3H,s),4.03(2H,t,J=6.5Hz),6.89(4H,s) [in CDCl₃] |
| 19 | 3-OMe | H | H | 3 | 2 | iPr | H | 2-OMe | H | free base, pale yellow oil, hydrochloride | 396 | 2225 (KBr) | 0.73,1.23(each 3H,d,J=6.5Hz),3.81,3.85(each 3H,s),4.22(2H,t,J=5.0Hz),6.99(4H,s),7.36(1H,t,J=8.5Hz) [in CD₃OD] |
| 20 | 3-OMe | H | H | 3 | 2 | iPr | Me | 2-OMe | H | free base, colorless oil | 410 | 2230 (liq) | 0.78,1.18(each 3H,d,J=6.5Hz),2.21(3H,s),3.80,3.84(each 3H,s),4.06(2H,t,J=6.5Hz),6.89(4H,s),7.27(1H,t,J=8.5Hz) [in CDCl₃] |
| 21 | 4-OMe | H | H | 3 | 2 | iPr | H | 2-OMe | H | free base, colorless oil | 396 | 2230 (liq) | 0.78,1.17(each 3H,d,J=6.5Hz),3.80,3.83(each 3H,s),4.08(2H,t,J=5.5Hz),6.87,7.27(each 2H,d,J=9.0Hz),6.89(4H,s) [in CDCl₃] |
| 22 | 4-OMe | H | H | 3 | 2 | iPr | Me | 2-OMe | H | free base, | 410 | 2230 (liq) | 0.77,1.16(each 3H,d,J=6.5Hz),2.21(3H,s),3.80,3.84(each 3H,s), |

TABLE 4-continued $$\underset{R_2}{\underset{R_1}{\bigcirc}}\overset{R_3}{\underset{C}{\overset{CN}{-}}}(CH_2)_m-\underset{R_4}{\overset{R_5}{N}}-(CH_2)_n-O-\underset{R_7}{\overset{R_6}{\bigcirc}}$$

| Example No. | $R_1$ | $R_2$ | $R_3$ | m | n | $R_4$ | $R_5$ | $R_6$ | $R_7$ | salt | Mass ($M^+$) | IR cm$^{-1}$ (CN) | NMR δ ppm |
|---|---|---|---|---|---|---|---|---|---|---|---|---|---|
| 23 | 2-OMe | H | H | 3 | 3 | iPr | H | 2-OMe | H | free base, colorless oil | 410 | 2230 (liq) | 4.06(2H,t,J=6.0Hz),6.89(4H,s),6.86,7.27(each 2H,d,J=9.0Hz) [in CDCl$_3$] |
| 24 | 2-OMe | H | H | 3 | 3 | iPr | Me | 2-OMe | H | free base, pale yellow oil | 424 | 2225 (liq) | 0.75,1.17(each 3H,d,J=7.0Hz),3.80(6H,s),4.05(2H,t,J=6.0Hz),6.88 (4H,s) [in CDCl$_3$] |
| 25 | 3-OMe | H | H | 3 | 3 | iPr | H | 2-OMe | H | free base, pale yellow oil | 410 | 2230 (liq) | 0.75,1.16(each 3H,d,J=7.0Hz),2.10(3H,s),3.79,3.85(each 3H,s), 6.89(4H,s) [in CDCl$_3$] |
| 26 | 3-OMe | H | H | 3 | 3 | iPr | Me | 2-OMe | H | free base, colorless oil | 424 | 2230 (liq) | 4.02(2H,t,J=6.5Hz),3.80(6H,s),4.06(2H,t,J=6.0Hz),6.88 (4H,s),7.27(1H,t,J=8.5Hz) [in CDCl$_3$] |
| 27 | 4-OMe | H | H | 3 | 3 | iPr | H | 2-OMe | H | free base, colorless oil | 410 | 2230 (liq) | 0.78,1.18(each 3H,d,J=6.5Hz),3.80(6H,s),3.80,3.85(each 3H,s), 4.03(2H,t,J=6.5Hz),6.89(4H,d,J=6.5Hz),7.27(1H,t,J=8.5Hz) [in CDCl$_3$] |
| 28 | 4-OMe | H | H | 3 | 3 | iPr | Me | 2-OMe | H | free base, pale yellow oil | 424 | 2240 (liq) | 0.77,1.16(each 3H,d,J=6.5Hz),6.89(4H,s),7.27(1H,t,J=8.5Hz) [in CDCl$_3$] 6.0Hz),6.86(2H,d,J=9.0Hz),6.88(4H,s),7.27(2H,d,J=9.0Hz) [in CDCl$_3$] |
| 29 | 4-OMe | H | H | 3 | 3 | iPr | H | 4-F | H | free base, colorless oil | 398 | 2230 (liq) | 0.76,1.15(each 3H,d,J=6.5Hz),6.86(2H,d,J=9.0Hz),7.26(2H,d,J=9.0Hz) [in CDCl$_3$] 4.03(2H,t,J=6.5Hz),3.80(3H,s),3.96(2H,t,J=6.0Hz),6.87, 7.27(each 2H,d,J=9.0Hz) [in CDCl$_3$] |
| 30 | 4-OMe | H | H | 3 | 3 | iPr | Me | 4-F | H | free base, colorless oil | 412 | 2225 (liq) | 0.76,1.14(each 3H,d,J=6.5Hz),2.11(3H,s),3.80(3H,s),3.93(2H,t,J=6.5Hz),6.87,7.26(each 2H,d,J=9.0Hz) [in CDCl$_3$] |
| 31 | 3-OMe | 4-OMe | H | 3 | 2 | iPr | H | H | H | free base | 397 (M+1) | 2230 (liq) | 0.80,1.18(each 3H,d,J=6.5Hz),3.87(6H,s),3.99(2H,t,J=5.0Hz) [in CDCl$_3$] |
| 32 | 3-OMe | 4-OMe | H | 3 | 2 | iPr | Me | H | H | free base, colorless oil | 410 | 2230 (liq) | 0.79,1.18(each 3H,d,J=7.0Hz),2.24(3H,s),3.87(6H,s),4.02(2H,t,J=6.0Hz) [in CDCl$_3$] |
| 33 | 3-OMe | 4-OMe | H | 3 | 2 | iPr | H | 4-F | H | free base, pale yellow oil | 414 | 2240 (liq) | 0.80,1.19(each 3H,d,J=6.5Hz),3.88(6H,s),3.98(2H,t,J=5.5Hz) [in CDCl$_3$] |
| 34 | 3-OMe | 4-OMe | H | 3 | 2 | iPr | Me | 4-F | H | free base, pale yellow oil | 428 | 2230 (liq) | 0.80,1.19(each 3H,d,J=6.5Hz),2.22(3H,s),3.87(6H,s),3.97(2H,t,J=6.0Hz) [in CDCl$_3$] |
| 35 | 3-OMe | 4-OMe | H | 3 | 2 | iPr | H | 3-F | H | pale yellow oil hydrochloride | 414 | 2240 (KBr) | 0.78,1.21(each 3H,d,J=6.5Hz),3.83,3.84(each 3H,d,J=5.0Hz) [in CD$_3$OD] |
| 36 | 3-OMe | 4-OMe | H | 3 | 2 | iPr | Me | 3-F | H | free base, pale yellow oil | 428 | 2230 (liq) | 0.79,1.18(each 3H,d,J=6.5Hz),2.22(3H,s),3.87(6H,s),3.99(2H,t,J=5.5Hz) [in CDCl$_3$] |
| 37 | 3-OMe | 4-OMe | H | 3 | 2 | iPr | H | 2-F | H | free base, oxalate | 414 | 2240 (KBr) | 0.78,1.20(each 3H,d,J=6.5Hz),3.82,3.84(each 3H,s),4.29(2H,t,J=5.5Hz) [in CD$_3$OD] |
| 38 | 3-OMe | 4-OMe | H | 3 | 2 | iPr | Me | 2-F | H | free base, pale yellow oil | 428 | 2240 (liq) | 0.78,1.17(each 3H,d,J=6.5Hz),2.22(3H,s),3.87(6H,s),4.08(2H,t,J=6.0Hz) [in CDCl$_3$] |
| 39 | 3-OMe | 4-OMe | H | 3 | 2 | iPr | H | 4-Cl | H | pale yellow oil hydrochloride | 430,432 (3:1) | 2240 (KBr) | 0.78,1.22(each 3H,d,J=7.0Hz),3.83,3.84(each 3H,s),4.21(2H,t,J=5.0Hz) [in CD$_3$OD] |
| 40 | 3-OMe | 4-OMe | H | 3 | 2 | iPr | Me | 4-Cl | H | free base, pale yellow oil | 444,446 (3:1) | 2220 (liq) | 0.79,1.18(each 3H,d,J=6.5Hz),2.22(3H,s),3.87(6H,s),3.98(2H,t,J=5.5Hz) [in CDCl$_3$] |
| 41 | 3-OMe | 4-OMe | H | 3 | 2 | iPr | H | 3-Cl | H | free base, pale yellow oil | 430,432 (3:1) | 2230 (liq) | 0.78,1.22(each 3H,d,J=6.5Hz),3.83,3.84(each 3H,s),4.23(2H,t,J=5.0Hz) [in CDCl$_3$] |
| 42 | 3-OMe | 4-OMe | H | 3 | 2 | iPr | Me | 3-Cl | H | free base pale yellow oil | 444,446 (3:1) | 2220 (liq) | 0.79,1.18(each 3H,d,J=6.5Hz),2.22(3H,s),3.87(6H,s),4.00(2H,t,J=5.5Hz) [in CD$_3$OD] |
| 43 | 3-OMe | 4-OMe | H | 3 | 2 | iPr | H | 4-Me | H | pale yellow oil hydrochloride | 410 | 2230 (KBr) | 0.78,1.21(each 3H,d,J=7.0Hz),2.25(3H,s),3.82,3.84(each 3H,s), |

TABLE 4-continued

Structure:

$$\begin{array}{c} CN \\ | \\ R_1-\text{Ar}-C-(CH_2)_m-N-(CH_2)_n-\text{Ar'}-O-R_7 \\ | \qquad | \\ R_4 \qquad R_5 \\ (R_2, R_3 \text{ on first ring; } R_6 \text{ on second ring}) \end{array}$$

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 44 | 3-OMe | 4-OMe | H | 3 | 2 | iPr | Me | 4-Me | H | free base, pale yellow oil | 424 | 2230 (liq) | 4.18(2H,t,J=5.5Hz),6.83(2H,d,J=9.0Hz),7.14(2H,d,J=9.0Hz) [in CD₃OD] 0.78,1.18(each 3H,d,J=6.5Hz),2.22(3H,s),2.27(3H,s),3.86(6H,s), 3.99(,2H,t,J=5.5Hz),6.77(2H,d,J=9.0Hz),7.06(2H,d,J=9.0Hz) [in CDCl₃] |
| 45 | 3-OMe | 4-OMe | H | 3 | 2 | iPr | H | 3-Me | H | free base, pale yellow oil | 410 | 2230 (liq) | 0.80,1.19(each 3H,d,J=6.5Hz),2.32(3H,s),3.87(6H,s),4.00(2H,t,J=5.5Hz) [in CDCl₃] |
| 46 | 3-OMe | 4-OMe | H | 3 | 2 | iPr | Me | 3-Me | H | free base, pale yellow oil | 424 | 2230 (liq) | 0.79,1.18(each 3H,d,J=6.5Hz),2.22(3H,s),2.32(3H,s),3.87(6H,s), 4.00(2H,t,J=5.0Hz) [in CDCl₃] |
| 47 | 3-OMe | 4-OMe | H | 3 | 2 | iPr | H | 4-OMe | H | free base, pale yellow oil | 440 | 2230 (liq) | 0.80,1.19(each 3H,d,J=6.5Hz),2.22(3H,s),3.76(3H,s),3.87(6H,s), 3.97(2H,t,J=6.0Hz) [in CDCl₃] |
| 48 | 3-OMe | 4-OMe | H | 3 | 2 | iPr | Me | 3-OMe | H | free base, pale yellow oil | 426 | 2230 (liq) | 0.80,1.19(each 3H,d,J=6.5Hz),3.78(3H,s),3.87(6H,s),4.01(2H,t,J=5.5Hz) [in CDCl₃] |
| 49 | 3-OMe | 4-OMe | H | 3 | 2 | iPr | Me | 3-CF₃ | H | hydrochloride (KBr) | 464 | 2230 (KBr) | 0.78,1.21(each 3H,d,J=6.5Hz),3.83,3.85(each 3H,s),3.87(6H,s),4.30(2H,d,J=5.0Hz) [in CD₃OD] |
| 50 | 3-OMe | 4-OMe | H | 3 | 2 | iPr | H | 3-CF₃ | H | free base, pale yellow oil | 478 | 2230 (liq) | 0.79,1.18(each 3H,d,J=6.5Hz),2.24(3H,s),3.87(6H,s),4.05(2H,t,J=5.5Hz) [in CDCl₃] |
| 51 | 3-OMe | 4-OMe | H | 3 | 2 | iPr | Me | 3-Me | 4-Me | hydrochloride | 424 | 2230 (KBr) | 0.78,1.21(each 3H,d,J=6.5Hz),2.17,2.22(each 3H,s),3.82,3.84(each 3H,s),4.16(2H,d,J=5.0Hz) [in CD₃OD] |
| 52 | 3-OMe | 4-OMe | H | 3 | 2 | iPr | H | 3-Me | 4-Cl | hydrochloride | 444 | 2230 (KBr) | 0.78,1.21(each 3H,d,J=6.5Hz),2.32(3H,s),3.82,3.84(each 3H,s),4.20(2H,t,J=5.0Hz) [in CD₃OD] |
| 53 | 3-OMe | 4-OMe | H | 3 | 2 | iPr | Me | 3-Me | 4-Cl | free base, pale yellow oil | 459 | 2230 (liq) | 0.78,1.20(each 3H,d,J=6.5Hz),2.23(3H,s),2.32(3H,s),3.87(6H,s),3.98(2H,t,J=5.5Hz) [in CDCl₃] |
| 54 | 3-OMe | 4-OMe | H | 3 | 2 | iPr | H | 3-OMe | 4-OMe | oxalate | 456 | 2230 (KBr) | 0.71,1.11(each 3H,d,J=6.5Hz),3.69,3.73,3.76,3.77(each 3H,s),4.12(2H,t,J=5.5Hz),6.44(1H,d-d,J=2.5,9.0Hz),6.62(1H,d,J=2.5Hz),6.85(1H,d,J=9.0Hz) [in DMSO-d₆] |
| 55 | 3-OMe | 4-OMe | H | 3 | 3 | iPr | H | 4-F | H | fumarate | 428 | 2225 (KBr) | 0.71,1.09(each 3H,d,J=6.5Hz),3.76,3.77(each 3H,s),3.98(2H,t,J=6.5Hz),6.49(2H,s) [in DMSO-d₆] |
| 56 | 3-OMe | 4-OMe | H | 3 | 3 | iPr | Me | 4-F | H | free base, yellow oil | 442 | 2225 (liq) | 0.78,1.16(each 3H,d,J=6.5Hz),2.11(3H,s),3.87,3.88(each 3H,s),3.93(2H,t,J=6.5Hz) [in CDCl₃] |
| 57 | 3-OMe | 4-OMe | H | 3 | 3 | iPr | H | 2-OMe | H | free base, pale yellow oil | 440 | 2230 (liq) | 0.79,1.18(each 3H,d,J=6.5Hz),3.80(3H,s),3.87,3.88(each 3H,s),4.07(2H,t,J=6.5Hz) [in CDCl₃] |
| 58 | 3-OMe | 4-OMe | H | 3 | 3 | iPr | Me | 2-OMe | H | free base, pale yellow oil | 454 | 2230 (liq) | 0.78,1.16(each 3H,d,J=6.5Hz),2.14(3H,s),3.85(3H,s),3.87,3.88(each 3H,s),4.04(2H,t,J=6.5Hz),6.89(4H,s) [in CDCl₃] |
| 59 | 3-OMe | 4-OMe | H | 3 | 3 | Me | H | 4-F | H | free base, pale yellow oil | 400 | 2230 (liq) | 1.70(3H,s),3.87,3.90(each 3H,s),3.97(2H,t,J=6.0Hz) [in CDCl₃] |
| 60 | 3-OMe | 4-OMe | 5-OMe | 2 | 2 | Me | Me | 4-F | H | free base, pale yellow oil | 414 | 2230 (liq) | 1.67(3H,s),2.15(3H,s),3.87,3.89(each 3H,s),3.94(2H,t,J=6.0Hz) [in CDCl₃] |
| 61 | 3-OMe | 4-OMe | 5-OMe | 2 | 2 | iPr | Me | 4-F | H | free base, pale yellow oil | 426 | 2230 (liq) | 0.81,1.20(each 3H,d,J=6.5Hz),2.32(3H,s),3.84(9H,s),3.98(2H,t,J=5.5Hz),6.58(2H,s) [in CDCl₃] |
| 62 | 3-OMe | 4-OMe | 5-OMe | 2 | 2 | iPr | H | 2-OMe | H | free base, pale yellow oil | 442 | 2230 (liq) | 0.79,1.21(each 3H,d,J=6.5Hz),3.84,3.85(each 3H,s),3.89(6H,s),4.05(2H,t,J=5.0Hz),6.59(2H,s),6.89(4H,s) [in CDCl₃] |
| 63 | 3-OMe | 4-OMe | 5-OMe | 2 | 2 | iPr | Me | 2-OMe | H | free base, pale yellow oil | 456 | 2240 (liq) | 0.81,1.21(each 3H,d,J=6.5Hz),2.33(3H,s),3.84(3H,s),3.85(6H,s),6.88(4H,s),6.58(2H,s) [in CDCl₃] |
| 64 | 3-OMe | 4-OMe | 5-OMe | 2 | 3 | Me | H | 2-OMe | H | hydrochloride | 428 | 2230 (KBr) | 1.81(3H,s),3.76(3H,s),3.83(3H,s),3.87(3H,s),4.13(2H,t,J=6.0Hz), |

TABLE 4-continued

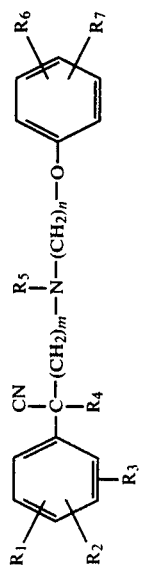

| Example No. | $R_1$ | $R_2$ | $R_3$ | m | n | $R_4$ | $R_5$ | $R_6$ | $R_7$ | salt | Mass (M+) | IR cm$^{-1}$ (CN) | NMR δ ppm |
|---|---|---|---|---|---|---|---|---|---|---|---|---|---|
| 65 | 3-OMe | 4-OMe | 5-OMe | 2 | 3 | Me | Me | 2-OMe | H | free base, pale yellow oil | 442 | 2230 (liq) | 6.80(2H,s) [in CD$_3$OD] 1.70(3H,s),2.24(3H,s),3.84(3H,s),3.85(3H,s),3.86(6H,s),4.04(2H,t,J=6.0Hz),6.63(2H,s),6.89(4H,s) [in CDCl$_3$] |
| 66 | 3-OMe | 4-OMe | 5-OMe | 2 | 3 | Et | H | 2-OMe | H | hydrochloride | 442 | 2220 (KBr) | 0.94(3H,t,J=7.0Hz),2.21(2H,q,J=7.0Hz),3.77(3H,s),3.83(3H,s),3.87(6H,s),4.13(2H,t,J=5.5Hz),6.76(2H,s) [in CD$_3$OD] |
| 67 | 3-OMe | 4-OMe | 5-OMe | 2 | 3 | Et | Me | 2-OMe | H | free base | 456 | 2220 (KBr) | 0.91(3H,t,J=7.0Hz),2.23(3H,S),3.84(6H,s),3.86(6H,s),4.03(2H,t,J=6.0Hz),6.58(2H,s),6.89(4H,s) |
| 68 | 3-OMe | 4-OMe | 5-OMe | 2 | 3 | nPr | H | 2-OMe | H | hydrochloride | 455 | 2225 (KBr) | 3.77(3H,s),3.83(3H,s),3.87(3H,s),4.13(2H,t,J=5.5Hz),6.76(2H,s) [in CD$_3$OD] |
| 69 | 3-OMe | 4-OMe | 5-OMe | 2 | 3 | nPr | Me | 2-OMe | H | free base | 470 | 2230 (KBr) | 2.22(3H,s),3.84(3H,s),3.85(3H,s),3.86(6H,s),4.03(2H,t,J=5.5Hz),6.59(2H,s),6.89(4H,s) [in CDCl$_3$] |
| 70 | 3-OMe | 4-OMe | 5-OMe | 2 | 3 | nBu | H | 2-OMe | H | hydrochloride | 470 | 2225 (KBr) | 3.77(3H,s),3.84(3H,s),3.87(6H,s),4.13(2H,t,J=5.5Hz),6.76(2H,s) [in CD$_3$OD] |
| 71 | 3-OMe | 4-OMe | 5-OMe | 2 | 3 | nBu | Me | 2-OMe | H | free base, pale yellow oil | 484 | 2220 (liq) | 2.22(3H,s),3.84(3H,s),3.86(9H,s),4.03(2H,t,J=6.5Hz),6.58(2H,s),6.89(4H,s) [in CDCl$_3$] |
| 72 | 3-OMe | 4-OMe | 5-OMe | 2 | 3 | iBu | H | 2-OMe | H | hydrochloride | 470 | 2225 (KBr) | 0.75(3H,d,J=6.5Hz),1.04(3H,d,J=6.5Hz),3.81(3H,s),3.85(3H,s),3.89(6H,s),4.14(2H,t,J=5.5Hz),6.77(2H,s),6.95(4H,s) [in CD$_3$OD] |
| 73 | 3-OMe | 4-OMe | 5-OMe | 2 | 3 | iBu | Me | 2-OMe | H | free base | 484 | 2230 (KBr) | 0.71(3H,d,J=6.5Hz),0.99(3H,d,J=6.5Hz),2.21(3H,s),3.84(3H,s),3.85(3H,s),3.86(2H,s),6.61(2H,s),6.89(4H,s) [CDCl$_3$] |
| 74 | 3-OMe | 4-OMe | 5-OMe | 3 | 2 | iPr | Me | H | H | free base, pale yellow oil | 440 | 2230 (liq) | 0.81,1.20(each 3H,d,J=6.5Hz),2.25(3H,s),3.84(9H,s),4.03(2H,t,J=5.5Hz),6.58(2H,s) [in CDCl$_3$] |
| 75 | 3-OMe | 4-OMe | 5-OMe | 3 | 2 | iPr | H | 4-F | H | hydrochloride | 444 | 2245 (liq) | 0.82,1.21(each 3H,d,J=6.5Hz),3.85(9H,s),3.98(2H,t,J=5.5Hz),6.57(2H,s) [in CDCl$_3$] |
| 76 | 3-OMe | 4-OMe | 5-OMe | 3 | 2 | iPr | Me | 4-F | H | free base, pale yellow oil | 458 | 2220 (liq) | 0.80,1.19(each 3H,d,J=6.5Hz),2.22(3H,s),3.85(9H,s),3.97(2H,t,J=5.5Hz),6.57(2H,s) [in CDCl$_3$] |
| 77 | 3-OMe | 4-OMe | 5-OMe | 3 | 2 | iPr | H | 4-Cl | H | free base, yellow oil | 460 | 2230 (liq) | 0.82,1.21(each 3H,d,J=6.5Hz),3.85(9H,s),3.93(2H,t,J=9.0Hz),7.25(2H,d,J=9.0Hz) [in CDCl$_3$] |
| 78 | 3-OMe | 4-OMe | 5-OMe | 3 | 2 | iPr | Me | 4-Cl | H | free base, pale yellow oil | 474,476 (3:1) | 2220 (liq) | 0.81,1.19(each 3H,d,J=6.5Hz),2.22(3H,s),3.85(9H,s),3.98(2H,t,J=5.5Hz),6.58(2H,s),6.80,7.22(each 2H,d,J=9.0Hz) [in CDCl$_3$] |
| 79 | 3-OMe | 4-OMe | 5-OMe | 3 | 2 | iPr | H | 4-Cl | H | hydrochloride | 440 | 2230 (KBr) | 0.80,1.23(each 3H,d,J=6.5Hz),2.30(3H,s),3.76(3H,s),3.85(6H,s),4.19(2H,t,J=5.0Hz),6.73(2H,s) [in CD$_3$OD] |
| 80 | 3-OMe | 4-OMe | 5-OMe | 3 | 2 | iPr | Me | 3-Me | H | free base | 454 | 2220 (liq) | 0.81,1.19(each 3H,d,J=6.5Hz),2.22(3H,s),2.32(3H,s),3.85(9H,s),4.00(2H,t,J=5.5Hz),6.58(2H,s) [in CDCl$_3$] |
| 81 | 3-OMe | 4-OMe | 5-OMe | 3 | 2 | iPr | H | 3-Me | H | hydrochloride | 440 | 2230 (liq) | 0.80,1.23(each 3H,d,J=6.5Hz),2.22(3H,s),3.76(3H,s),3.86(6H,s),6.74(2H,s) [in CD$_3$OD] |
| 82 | 3-OMe | 4-OMe | 5-OMe | 3 | 2 | iPr | Me | 2-Me | H | free base, pale yellow oil | 454 | 2230 (liq) | 0.80,1.19(each 3H,d,J=6.5Hz),2.20(3H,s),2.24(3H,s),3.85(9H,s),4.02(2H,t,J=5.5Hz),6.58(2H,s) [in CDCl$_3$] |
| 83 | 3-OMe | 4-OMe | 5-OMe | 3 | 2 | iPr | H | 3-OMe | H | hydrochloride | 456 | 2230 (KBr) | 0.80,1.24(each 3H,d,J=6.5Hz),3.76(6H,s),3.85(6H,s),4.21(2H,t,J=5.0Hz),6.73(2H,s) [in CD$_3$OD] |
| 84 | 3-OMe | 4-OMe | 5-OMe | 3 | 2 | iPr | H | 2-OMe | H | free base, pale yellow oil | 456 | 2230 (liq) | 0.81,1.20(each 3H,d,J=6.5Hz),3.83,3.84(each 3H,s)3.85(6H,s),4.08(2H,t,J=5.5Hz),6.58(2H,s) [in CDCl$_3$] |
| 85 | 3-OMe | 4-OMe | 5-OMe | 3 | 2 | iPr | Me | 2-OMe | H | free base, pale yellow oil | 470 | 2230 (liq) | 0.80,1.19(each 3H,d,J=6.5Hz),2.24(3H,s),3.85(9H,s),4.08(2H,t,J=6.0Hz),6.59(2H,s),6.89(4H,s) [in CDCl$_3$] |

TABLE 4-continued

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 86 | 3-OMe | 4-OMe | 5-OMe | 3 | 2 | iPr | H | 2-OMe | 6-OMe | hydrochloride | 486 | 2225 (KBr) | 0.81(3H,d,J=6.5Hz),1.24(3H,d,J=6.5Hz),3.77(3H,s),3.80(6H,s),3.86 (6H,s),4.12(2H,t,J=5.0Hz),6.75(2H,s) [in CD₃OD] |
| 87 | 3-OMe | 4-OMe | 5-OMe | 3 | 2 | iPr | H | 2-OEt | H | hydrochloride | 470 | 2230 (KBr) | 0.80(3H,d,J=7.0Hz),1.24(3H,d,J=7.0Hz),1.39(3H,t,J=7.0Hz)3.76 (3H,s),3.86(6H,s),4.10(2H,q,J=7.0Hz),4.22(2H,t,J=5.5Hz),6.74(2H, s),6.98(4H,s) [in CD₃OD] |
| 88 | 3-OMe | 4-OMe | 5-OMe | 3 | 2 | Me | H | 2-OMe | H | fumarate | 428 | 2230 (KBr) | 1.76(3H,s),3.75(3H,s),3.85(9H,s),4.22(2H,t,J=5.0Hz),6.67(2H,s), 6.77(2H,s) [in CD₃OD] |
| 89 | 3-OMe | 4-OMe | 5-OMe | 3 | 2 | Me | Me | 2-OMe | H | hydrochloride | 442 | 2230 (KBr) | 1.77(3H,s),2.97(3H,s),3.75(3H,s),3.84(3H,s),3.86(6H,s),4.31(2H,t, J=5.0Hz),6.79(2H,s) [in CD₃OD] |
| 90 | 3-OMe | 4-OMe | 5-OMe | 3 | 2 | Et | H | 2-OMe | H | free base, yellow oil | 442 | 2220 (liq) | 0.94(3H,t,J=7.0Hz),3.83(3H,s),3.85(3H,s),3.86(6H,s),4.09(2H,t, J=5.5Hz),6.59(2H,s),6.90(4H,s) [in CDCl₃] |
| 91 | 3-OMe | 4-OMe | 5-OMe | 3 | 2 | nPr | H | 2-OMe | H | fumarate | 456 | 2225 (KBr) | 0.91(3H,t,J=6.5Hz),3.76(3H,s),3.85(9H,s),4.22(2H,t,J=5.5Hz),6.67 (2H,s),6.74(2H,s) [in CD₃OD] |
| 92 | 3-OMe | 4-OMe | 5-OMe | 3 | 2 | nBu | H | 2-OMe | H | free base, pale yellow oil | 470 | 2220 (liq) | 3.83,3.85(each 3H,s),3.86(6H,s),4.09(2H,t,J=5.0Hz),6.59(2H,s), 6.90(4H,s) [in CDCl₃] |
| 93 | 3-OMe | 4-OMe | 5-OMe | 3 | 2 | iBu | H | 2-OMe | H | fumarate | 470 | 2220 (KBr) | 0.73(3H,d,J=6.0Hz),1.02(3H,d,J=6.0Hz),3.76(3H,s),3.85(9H,s),4.21 (2H,t,J=5.0Hz),6.67(2H,s),6.76(2H,s) [in CD₃OD] |
| 94 | 3-OMe | 4-OMe | 5-OMe | 3 | 3 | iPr | H | H | H | oxalate | 440 | 2230 (KBr) | 0.79,1.22(each 3H,d,J=6.5Hz),3.75(3H,s),3.84(6H,s),4.05(2H,t,J= 5.5Hz),6.72(2H,s) [in CD₃OD] |
| 95 | 3-OMe | 4-OMe | 5-OMe | 3 | 3 | iPr | Me | H | H | free base, pale yellow oil | 454 | 2230 (liq) | 0.80,1.17(each 3H,d,J=6.5Hz),2.12(3H,s),3.85(3H,s),3.86(6H,s), 3.98(2H,t,J=6.5Hz),6.57(2H,s) [in CDCl₃] |
| 96 | 3-OMe | 4-OMe | 5-OMe | 3 | 3 | iPr | H | 4-F | H | free base, yellow oil | 458 | 2230 (liq) | 0.81,1.20(each 3H,d,J=6.5Hz),3.85(3H,s),3.86(6H,s),3.96(2H,t,J= 6.0Hz),6.57(2H,s) [in CDCl₃] |
| 97 | 3-OMe | 4-OMe | 5-OMe | 3 | 3 | iPr | Me | 4-F | H | free base, pale yellow oil | 472 | 2230 (liq) | 0.80,1.17(each 3H,d,J=6.5Hz),2.12(3H,s),3.85(3H,s),3.86(6H,s), 3.94(2H,t,J=6.5Hz),6.57(2H,s) [in CDCl₃] |
| 98 | 3-OMe | 4-OMe | 5-OMe | 3 | 3 | iPr | H | 3-F | H | fumarate | 458 | 2230 (KBr) | 0.79,1.22(each 3H,d,J=6.5Hz),3.75(3H,s),3.85(6H,s),4.05(2H,t,J= 6.0Hz),6.67(2H,s),6.72(2H,s) [in CD₃OD] |
| 99 | 3-OMe | 4-OMe | 5-OMe | 3 | 3 | iPr | Me | 3-F | H | oxalate | 472 | 2230 (KBr) | 0.79,1.22(each 3H,d,J=6.5Hz),2.80(3H,s),3.75(3H,s),3.85(6H,s), 4.03(2H,t,J=6.0Hz),6.73(2H,s) [in CD₃OD] |
| 100 | 3-OMe | 4-OMe | 5-OMe | 3 | 3 | iPr | H | 2-F | H | fumarate | 458 | 2230 (KBr) | 0.80,1.23(each 3H,d,J=6.5Hz),3.75(3H,s),3.85(6H,s),4.14(2H,t,J= 5.5Hz),6.67(2H,s),6.72(2H,s) [in CD₃OD] |
| 101 | 3-OMe | 4-OMe | 5-OMe | 3 | 3 | iPr | Me | 2-F | H | oxalate | 472 | 2230 (KBr) | 0.79,1.22(each 3H,d,J=5.5Hz),2.81(3H,s),3.75(3H,s),3.85(6H,s), 4.11(2H,t,J=5.5Hz),6.73(2H,s) [in CD₃OD] |
| 102 | 3-OMe | 4-OMe | 5-OMe | 3 | 3 | iPr | H | 4-Cl | H | free base, yellow oil | 474 | 2230 (liq) | 0.81,1.20(each 3H,d,J=6.5Hz),3.85(3H,s),3.86(6H,s),3.97(2H,t,J= 6.0Hz),6.57(2H,s),6.79(2H,d,J=9.0Hz),7.21(2H,d,J=9.0Hz) [in CDCl₃] |
| 103 | 3-OMe | 4-OMe | 5-OMe | 3 | 3 | iPr | Me | 4-Cl | H | free base, pale yellow oil | 488,490 (3:1) | 2230 (liq) | 0.80,1.17(each 3H,d,J=6.5Hz),2.12(3H,s),3.85(3H,s),3.86(6H,s), 3.95(2H,t,J=6.0Hz),6.56(2H,s),6.80,7.21(each 2H,d,J=9.0Hz) [in CDCl₃] |
| 104 | 3-OMe | 4-OMe | 5-OMe | 3 | 3 | iPr | H | 3-Cl | H | fumarate | 474,476 (3:1) | 2230 (KBr) | 0.79,1.23(each 3H,d,J=6.5Hz),3.75(3H,s),3.85(6H,s),4.05(2H,t,J= 5.5Hz),6.67(2H,s),6.72(2H,s) [in CD₃OD] |
| 105 | 3-OMe | 4-OMe | 5-OMe | 3 | 3 | iPr | Me | 3-Cl | H | free base, yellow oil | 488,490 (3:1) | 2230 (KBr) | 0.80,1.18(each 3H,d,J=6.5Hz),2.13(3H,s),3.85(3H,s),3.86(6H,s), 3.97(2H,t,J=5.5Hz),6.57(2H,s) [in CDCl₃] |
| 106 | 3-OMe | 4-OMe | 5-OMe | 3 | 3 | iPr | H | 2-Cl | H | fumarate | 474,476 (3:1) | 2220 (KBr) | 0.80,1.23(each 3H,d,J=6.5Hz),3.75(3H,s),3.86(6H,s),4.16(2H,t,J= 5.5Hz),6.67(2H,s),6.72(2H,s) [in CD₃OD] |

TABLE 4-continued

Structure: R1, R2, R3 substituted phenyl — C(CN)(R4) — (CH2)m — N(R5) — (CH2)n — O — phenyl with R6, R7

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 107 | 3-OMe | 4-OMe | 5-OMe | 3 | 3 | iPr | Me | 2-Cl | H | free base, yellow oil | 482,490 (3:1) | 2230 (liq) | 0.79,1.16(each 3H,d,J=6.5Hz),2.14((3H,s),3.85(3H,s),3.86(6H,s),4.06(2H,t,J=6.5Hz),6.56(2H,s) [in CDCl₃] |
| 108 | 3-OMe | 4-OMe | 5-OMe | 3 | 3 | iPr | H | 4-Me | H | oxalate | 454 | 2230 (KBr) | 0.79,1.22(each 3H,d,J=6.5Hz),2.24(3H,s),3.75(3H,s),3.85(6H,s),4.01(2H,t,J=6.0Hz),6.72(2H,s),6.76,7.06(each 2H,d,J=8.5Hz) [in CD₃OD] |
| 109 | 3-OMe | 4-OMe | 5-OMe | 3 | 3 | iPr | Me | 4-Me | H | free base, yellow oil | 468 | 2240 (liq) | 0.80,1.18(each 3H,d,J=6.5Hz),2.14((3H,s),2.29(3H,s),3.85(3H,s),3.86(6H,s),3.95(2H,t,J=6.5Hz),6.57(2H,s)6.77,7.07(each 2H,d,J=9.0Hz) [in CDCl₃] |
| 110 | 3-OMe | 4-OMe | 5-OMe | 3 | 3 | iPr | H | 3-Me | H | free base, yellow oil | 454 | 2230 (liq) | 0.81,1.20(each 3H,d,J=6.5Hz),2.31(3H,s),3.85(3H,s),3.86(6H,s),3.99(2H,t,J=6.0Hz),6.57(2H,s) [in CDCl₃] |
| 111 | 3-OMe | 4-OMe | 5-OMe | 3 | 3 | iPr | Me | 3-Me | H | free base, pale yellow oil | 468 | 2230 (liq) | 0.80,1.17(each 3H,d,J=6.5Hz),2.11(3H,s),2.31(3H,s),3.85(3H,s),3.86(6H,s),3.96(2H,t,J=6.5Hz),6.57(2H,s) [in CDCl₃] |
| 112 | 3-OMe | 4-OMe | 5-OMe | 3 | 3 | iPr | H | 2-Me | H | free base, yellow oil | 454 | 2220 (liq) | 0.81,1.20(each 3H,d,J=7.0Hz),2.18(3H,s),3.85(3H,s),3.86(6H,s),4.01(2H,t,J=6.0Hz),6.57(2H,s) [in CDCl₃] |
| 113 | 3-OMe | 4-OMe | 5-OMe | 3 | 3 | iPr | Me | 2-Me | H | free base, pale yellow oil | 468 | 2230 (liq) | 0.80,1.17(each 3H,d,J=6.5Hz),2.12(3H,s),2.20(3H,s),3.84(3H,s),3.85(6H,s),3.98(2H,t,J=6.0Hz),6.56(2H,s) [in CDCl₃] |
| 114 | 3-OMe | 4-OMe | 5-OMe | 3 | 3 | iPr | H | 4-OMe | H | fumarate | 470 | 2230 (KBr) | 0.79,1.23(each 3H,d,J=6.5Hz),3.72,3.75(each 3H,s),3.85(6H,s),4.00(2H,t,J=6.0Hz),6.67(2H,s),6.82(4H,s) [in CD₃OD] |
| 115 | 3-OMe | 4-OMe | 5-OMe | 3 | 3 | iPr | Me | 4-OMe | H | oxalate | 424 | 2230 (KBr) | 0.79,1.22(each 3H,d,J=6.5Hz),2.80(3H,s),3.73,3.75(each 3H,s),3.85(6H,s),3.98(2H,t,J=6.0Hz),6.72(2H,s),6.82(4H,s) [in CD₃OD] |
| 116 | 3-OMe | 4-OMe | 5-OMe | 3 | 3 | iPr | H | 3-OMe | H | oxalate | 470 | 2230 (KBr) | 0.79,1.22(each 3H,d,J=6.5Hz),3.75(6H,s),3.85(6H,s),4.03(2H,t,J=6.0Hz),6.72(2H,s) [in CD₃OD] |
| 117 | 3-OMe | 4-OMe | 5-OMe | 3 | 3 | iPr | Me | 3-OMe | H | free base, yellow oil | 484 | 2230 (liq) | 0.79,1.17(each 3H,d,J=6.5Hz),2.13(3H,s),3.78,3.85(each 3H,s),3.86(6H,s),3.97(2H,t,J=5.5Hz),6.57(2H,s) [in CDCl₃] |
| 118 | 3-OMe | 4-OMe | 5-OMe | 3 | 3 | iPr | H | 2-OMe | H | free base, pale yellow oil | 470 | 2230 (liq) | 0.80,1.19(each 3H,d,J=6.5Hz),3.80,3.84(each 3H,s),3.86(6H,s),4.07(2H,t,J=6.0Hz),6.57(2H,s),6.88(4H,s) [in CDCl₃] |
| 119 | 3-OMe | 4-OMe | 5-OMe | 3 | 3 | iPr | Me | 2-OMe | H | free base, yellow oil | 484 | 2230 (liq) | 0.80,1.18(each 3H,d,J=6.5Hz),2.12(3H,s),3.86(12H,s),4.04(2H,t,J=6.5Hz),6.57(2H,s),6.89(4H,s) [in CDCl₃] |
| 120 | 3-OMe | 4-OMe | 5-OMe | 3 | 3 | iPr | H | 4-nPr | H | fumarate | 482 | 2220 (KBr) | 0.79,1.22(each 3H,d,J=6.5Hz),3.75(3H,s),3.85(6H,s),4.02(2H,t,J=5.5Hz),5.67(2H,s),6.72(2H,s),6.78,7.07(each 2H,d,J=8.5Hz) [in CD₃OD] |
| 121 | 3-OMe | 4-OMe | 5-OMe | 3 | 3 | iPr | Me | 4-nPr | H | oxalate | 496 | 2240 (KBr) | 0.77,1.22(each 3H,d,J=6.5Hz),2.80(3H,s),3.75(3H,s),3.85(6H,s)4.01(2H,t,J=6.0Hz),6.73(2H,s),6.78,7.08(each 2H,d,J=8.5Hz) [in CD₃OD] |
| 122 | 3-OMe | 4-OMe | 5-OMe | 3 | 3 | iPr | H | 2-nPr | H | fumarate | 482 | 2220 (KBr) | 0.79,1.22(each 3H,d,J=6.5Hz),3.75(3H,s),3.85(6H,s),4.04(2H,t,J=6.0Hz),6.67(2H,s),6.71(2H,s) [in CDCl₃] |
| 123 | 3-OMe | 4-OMe | 5-OMe | 3 | 3 | iPr | Me | 2-nPr | H | free base, yellow oil | 496 | 2230 (liq) | 0.80,1.18(each 3H,d,J=6.5Hz),2.14(3H,s),3.85(9H,s),3.98(2H,t,J=6.0Hz),6.57(2H,s) [in CDCl₃] |
| 124 | 3-OMe | 4-OMe | 5-OMe | 3 | 3 | iPr | H | 3-tBu | H | free base, yellow oil | 496 | 2230 (liq) | 0.81,1.20(each 3H,d,J=6.5Hz),1.30(9H,s),3.85(3H,s),3.86(6H,s),4.00(2H,t,J=5.5Hz),3.97(2H,s) [in CDCl₃] |
| 125 | 3-OMe | 4-OMe | 5-OMe | 3 | 3 | iPr | Me | 3-tBu | H | free base, yellow oil | 510 | 2230 (liq) | 0.80,1.17(each 3H,d,J=6.5Hz),1.30(9H,s),2.14(3H,s),3.85(3H,s),3.86(6H,s),3.98(2H,t,J=6.5Hz),6.57(2H,s) [in CDCl₃] |
| 126 | 3-OMe | 4-OMe | 5-OMe | 3 | 3 | iPr | H | 4-NH₂ | H | oxalate | 455 | 2200 (KBr) | 0.72,1.13(each 3H,d,J=6.0Hz),3.67(3H,s),3.80(6H,s),6.67(2H,s) [in DMSO-d₆] |
| 127 | 3-OMe | 4-OMe | 5-OMe | 3 | 3 | iPr | Me | 4-NH₂ | H | oxalate | 469 | 2225 (KBr) | 0.78,1.21(each 3H,d,J=7.0Hz),2.80(3H,s),3.75(3H,s),3.85(6H,s),4.00(2H,t,J=5.5Hz),6.72(2H,s) [in DMSO-d₆] |

TABLE 4-continued $$\begin{array}{c} R_1 \\ R_2 \\ R_3 \end{array} \cdot \begin{array}{c} CN \\ | \\ C-(CH_2)_m-N-(CH_2)_n-O- \\ | \\ R_4 \end{array} \cdot \begin{array}{c} R_5 \\ | \\ R_7 \end{array}$$

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 128 | 3-OMe | 4-OMe | 5-OMe | 3 | 3 | iPr | H | 3-NH₂ | H | oxalate | 455 | 2200 (KBr) | 0.71,1.12(each 3H,d,J=6.0Hz),3.67(3H,s),3.80(6H,s),6.67(2H,S) [in DMSO-d₆] |
| 129 | 3-OMe | 4-OMe | 5-OMe | 3 | 3 | iPr | Me | 3-NH₂ | H | oxalate | 469 | 2225 (KBr) | 0.79,1.21(each 3H,d,J=7.0Hz),2.80(3H,s),3.75(3H,s),3.84(6H,s),4.00 (2H,J=5.0Hz),6.72(2H,s) [in DMSO-d₆] |
| 130 | 3-OMe | 4-OMe | 5-OMe | 3 | 3 | iPr | H | 4-NO₂ | H | fumarate | 485 | 2210 (KBr) | 0.79,1.22(each 3H,d,J=6.5Hz),3.76(3H,s),3.85(6H,s),4.18(2H,t, J=5.5Hz),6.64(2H,S),6.71(2H,s),7.05,8.19(each 2H,d,J=9.0Hz) [in CD₃OD] |
| 131 | 3-OMe | 4-OMe | 5-OMe | 3 | 3 | iPr | Me | 4-NO₂ | H | free base, yellow oil | 499 | 2200 (liq) | 0.80,1.18(each 3H,d,J=6.5Hz),2.15(3H,s),3.85(6H,s),3.86(6H,s),4.08 (2H,t,J=6.0Hz),6.57(2H,s),6.94,8.19(each 2H,d,J=9.0Hz) [in CDCl₃] |
| 132 | 3-OMe | 4-OMe | 5-OMe | 3 | 3 | iPr | H | 3-NO₂ | H | fumarate | 485 | 2200 (KBr) | 0.79,1.22(each 3H,d,J=7.0Hz),3.75(3H,s),3.85(6H,s),4.16(2H,t, J=6.0Hz),6.65(2H,S),6.72(2H,s) [in CD₃OD] |
| 133 | 3-OMe | 4-OMe | 5-OMe | 3 | 3 | iPr | Me | 3-NO₂ | H | free base, yellow oil | 499 | 2200 (liq) | 0.80,1.17(each 3H,d,J=6.5Hz),2.14(3H,s),3.85(3H,s),3.86(6H,s),4.14 (2H,t,J=6.0Hz),6.57(2H,s) [in CDCl₃] |
| 134 | 3-OMe | 4-OMe | 5-OMe | 3 | 3 | iPr | H | 4-CH₂OH | H | fumarate | 470 | 2225 (KBr) | 0.79,1.22(each 3H,d,J=6.5Hz),3.75(3H,s),3.85(6H,s),4.05(2H,t,J=6.0Hz), 4.51(2H,s),6.67(2H,S),6.72(2H,S),6.86,7.26(each 2H,d,J=8.5Hz) [in CD₃OD] |
| 135 | 3-OMe | 4-OMe | 5-OMe | 3 | 3 | iPr | Me | 4-CH₂OH | H | fumarate | 484 | 2215 (liq) | 0.80,1.18(each 3H,d,J=7.0Hz),2.12(3H,s),3.85(9H,s),3.98(2H,t,J=6.0Hz), 4.60(2H,S),6.56(2H,S),6.86,7.27(each 2H,d,J=9.0Hz) [in CDCl₃] |
| 136 | 3-OMe | 4-OMe | 5-OMe | 3 | 3 | iPr | H | 3-CH₂OH | H | fumarate | 470 | 2240 (KBr) | 0.79,1.22(each 3H,d,J=6.0Hz),3.75(3H,S),3.85(6H,s),4.06(2H,t, J=6.0Hz),4.56(2H,s),6.66(2H,s),6.71(2H,s) [in CD₃OD] |
| 137 | 3-OMe | 4-OMe | 5-OMe | 3 | 3 | iPr | H | 2-CH₂OH | H | oxalate | 470 | 2215 (KBr) | 0.78,1.21(each 3H,d,J=7.0Hz),3.75(3H,s),3.85(6H,s),4.10(2H,t, J=6.0Hz),4.55(2H,s),6.71(2H,s) [in CDCl₃] |
| 138 | 3-OMe | 4-OMe | 5-OMe | 3 | 3 | iPr | H | 4-CN | H | fumarate | 465 | 2200 (KBr) | 0.79,1.22(each 3H,d,J=7.0Hz),3.76(3H,s),3.85(6H,s),4.14(2H,t, J=6.0Hz),6.65(2H,s),6.72(2H,s),7.04,7.64(each 2H,d,J=9.0Hz) [in CD₃OD] |
| 139 | 3-OMe | 4-OMe | 5-OMe | 3 | 3 | iPr | Me | 4-CN | H | free base, yellow oil | 479 | 2215 (liq) | 0.80,1.17(each 3H,d,J=7.0Hz),2.13(3H,s),3.85(9H,s),4.03(2H,t, J=6.0Hz),6.57(2H,S),6.93,7.58(each 2H,d,J=9.0Hz) [in CDCl₃] |
| 140 | 3-OMe | 4-OMe | 5-OMe | 3 | 3 | iPr | H | 4-OCH₂PR | H | fumarate | 546 | 2240 (KBr) | 0.79,1.22(each 3H,d,J=6.5Hz),3.75(3H,s),3.84(6H,s),3.99(2H,t,J=5.5Hz), 5.01(2H,S),6.67(2H,S),6.71(2H,s),6.79,6.92(each 2H,d,J=9.0Hz) [in CD₃OD] |
| 141 | 3-OMe | 4-OMe | 5-OMe | 3 | 3 | iPr | Me | 4-OCH₂PR | H | oxalate | 560 | 2240 (KBr) | 0.80,1.22(each 3H,d,J=7.0Hz),2.80(3H,s),3.75(3H,s),3.84(6H,s),3.98 (2H,t,J=5.5Hz),5.02(2H,s),6.72(2H,s),6.79,6.93(each 2H,d,J=9.0Hz) [in CDCl₃] |
| 142 | 3-OMe | 4-OMe | 5-OMe | 3 | 3 | iPr | H | 3-OCH₂PR | H | oxalate | 546 | 2240 (KBr) | 0.79,1.22(each 3H,d,J=7.0Hz),3.75(3H,s),3.84(6H,s),4.03(2H,t, J=6.0Hz),5.04(2H,s),6.71(2H,s) [in CDCl₃] |
| 143 | 3-OMe | 4-OMe | 5-OMe | 3 | 3 | iPr | Me | 3-OCH₂PR | H | fumarate | 560 | 2240 (liq) | 0.79,1.17(each 3H,d,J=6.5Hz),2.12(3H,s),3.84(3H,s),3.85(6H,s),3.96 (2H,t,J=6.0Hz),5.03(2H,S),6.57(2H,s) [in CDCl₃] |
| 144 | 3-OMe | 4-OMe | 5-OMe | 3 | 3 | iPr | H | 2-OCH₂PR | H | fumarate | 546 | 2240 (KBr) | 0.78,1.20(each 3H,d,J=6.5Hz),3.76(3H,s),3.81(6H,s),4.13(2H,t, J=5.5Hz),5.05(2H,s),6.68(4H,s) [in CD₃OD] |
| 145 | 3-OMe | 4-OMe | 5-OMe | 3 | 3 | iPr | Me | 2-OCH₂PR | H | free base, yellow oil | 560 | 2240 (liq) | 0.79,1.17(each 3H,d,J=6.5Hz),2.11(3H,s),3.85(9H,s),4.05(2H,t, J=6.0Hz),5.11(2H,S),6.56(2H,s),6.90(4H,S) [in CDCl₃] |
| 146 | 3-OMe | 4-OMe | 5-OMe | 3 | 3 | iPr | H | 3-OMe | 5-OMe | hydrochloride | 500 | 2220 (KBr) | 0.80(3H,d,J=7.0Hz),1.21(3H,d,J=7.0Hz),1.77(1H,s),3.74(6H,s),3.83 (3H,s),3.88(6H,s),3.98(2H,t,J=5.0Hz),6.05(3H,s),6.62(2H,s) [in CDCl₃] |
| 147 | 3-OMe | 4-OMe | 5-OMe | 3 | 3 | iPr | Me | 3-OMe | 5-OMe | free base, colorless oil | 514 | 2225 (liq) | 0.80(3H,d,J=7.0Hz),1.18(3H,d,J=7.0Hz),2.12(3H,s),3.76(6H,s),3.85 (3H,s),3.86(6H,s),3.95(2H,t,J=6.0Hz),6.07(3H,s),6.57(2H,s) [in CDCl₃] |

TABLE 4-continued

Structure:

$$\begin{array}{c} R_1 \\ R_2 \end{array} \!\!\!\!\!\! \diagram \!\!\!\!\!\! \begin{array}{c} CN \\ | \\ C-(CH_2)_m-N-(CH_2)_n-O \\ | \\ R_4 \end{array} \!\!\!\!\!\! \diagram \!\!\!\!\!\! \begin{array}{c} R_6 \\ R_7 \end{array}$$

with $R_3$ on first ring, $R_5$ on N.

| Example No. | $R_1$ | $R_2$ | $R_3$ | m | n | $R_4$ | $R_5$ | $R_6$ | $R_7$ | salt | Mass (M$^+$) | IR cm$^{-1}$ (CN) | NMR δ ppm |
|---|---|---|---|---|---|---|---|---|---|---|---|---|---|
| 148 | 3-OMe | 4-OMe | 5-OMe | 3 | 3 | iPr | H | 3-CH$_2$N(cyclohexyl ring) | H | free base, colorless oil | 537 | 2230 (liq) | 0.81,1.20(each 3H,d,J=6.5Hz),3.46(2H,s),3.85(3H,s),3.86(6H,s),4.01(2H,t,J=6.0Hz),6.57(2H,s) [in CDCl$_3$] |
| 149 | 3-OMe | 4-OMe | 5-OMe | 3 | 3 | iPr | Me | 3-CH$_2$N(cyclohexyl ring) | H | free base, colorless oil | 551 | 2230 (liq) | 0.79,1.18(each 3H,d,J=6.5Hz),2.12(3H,s),3.44(2H,s),3.85(3H,s),3.86(6H,s),4.00(2H,t,J=6.5Hz),6.57(2H,s) [in CDCl$_3$] |
| 150 | 3-OMe | 4-OMe | 5-OMe | 3 | 3 | iPr | H | 2-OEt | H | free base, pale yellow oil | 484 | 2230 (liq) | 0.80(3H,d,J=7.0Hz),1.19(3H,d,J=7.0Hz),1.39(3H,t,J=7.0Hz),1.86(1H,s),3.84(3H,s),3.86(6H,s),4.04(2H,q,J=7.0Hz),4.08(2H,t,J=7.0Hz),6.57(2H,s),6.88(4H,s) [in CDCl$_3$] |
| 151 | 3-OMe | 4-OMe | 5-OMe | 3 | 3 | iPr | Me | 2-OEt | H | free base, pale yellow oil | 498 | 2235 (liq) | 0.80(3H,d,J=7.0Hz),1.18(3H,d,J=7.0Hz),1.42(3H,t,J=7.0Hz),2.11(3H,s),3.84(3H,s),3.86(6H,s),4.03(2H,t,J=7.0Hz),4.07(2H,q,J=7.0Hz),6.57(2H,s),6.88(4H,s) [in CDCl$_3$] |
| 152 | 3-OMe | 4-OMe | 5-OMe | 3 | 3 | iPr | H | 3-Me | 5-Me | fumarate | 468 | 2230 (KBr) | 0.79(3H,d,J=7.0Hz),1.22(3H,d,J=7.0Hz),2.23(6H,s),3.75(3H,s),3.85(6H,s),4.00(2H,t,J=6.0Hz),6.51(2H,s),6.57(1H,s),6.66(2H,s),6.71(2H,s) [in CD$_3$OD] |
| 153 | 3-OMe | 4-OMe | 5-OMe | 3 | 3 | iPr | Me | 3-Me | 5-Me | free base, colorless oil | 482 | 2230 (liq) | 0.80(3H,d,J=7.0Hz),1.18(3H,d,J=7.0Hz),2.12(3H,s),2.28(6H,s),3.85(3H,s),3.86(6H,s),3.95(2H,t,J=6.0Hz),6.53(2H,s),6.58(3H,s) [in CDCl$_3$] |
| 154 | 3-OMe | 4-OMe | 5-OMe | 3 | 3 | iPr | Et | 4-F | H | free base, pale yellow oil | 486 | 2225 (liq) | 0.81,1.18(each 3H,d,J=6.5Hz),0.94(3H,t,J=7.0Hz),3.84(3H,s),3.85(6H,s),3.92(2H,t,J=6.5Hz),6.56(2H,s) [in CDCl$_3$] |
| 155 | 3-OMe | 4-OMe | 5-OMe | 3 | 3 | iPr | nPr | 4-F | H | free base, pale yellow oil | 500 | 2230 (liq) | 0.80,1.17(each 3H,d,J=6.5Hz),0.82(3H,t,J=6.0Hz),3.84(3H,s),3.85(6H,s),3.92(2H,t,J=6.5Hz),6.57(2H,s) [in CDCl$_3$] |
| 156 | 3-OMe | 4-OMe | 5-OMe | 3 | 3 | iPr | Et | 2-OMe | H | free base, pale yellow oil | 498 | 2220 (liq) | 0.80(3H,d,J=7.0Hz),0.95(3H,t,J=7.0Hz),1.18(3H,d,J=7.0Hz),3.84(6H,s),3.85(6H,s),4.03(2H,t,J=7.0Hz),6.57(2H,s),6.89(4H,s) [in CDCl$_3$] |
| 157 | 3-OMe | 4-OMe | 5-OMe | 3 | 3 | iPr | nPr | 2-OMe | H | free base, pale yellow oil | 512 | 2225 (liq) | 0.80(3H,d,J=7.0Hz),0.82(3H,t,J=7.0Hz),1.18(3H,d,J=7.0Hz),3.84(6H,s),3.86(6H,s),4.03(2H,t,J=7.0Hz),6.57(2H,s),6.89(4H,s) [in CDCl$_3$] |
| 158 | 3-OMe | 4-OMe | 5-OMe | 3 | 3 | Me | H | 4-F | H | fumarate | 430 | 2240 (KBr) | 1.67(3H,s),3.69(3H,s),3.81(6H,s),4.00(3H,t,J=7.0Hz),6.57(2H,s),6.89(4H,s),4.00(3H,t,J=6.0Hz),6.50(2H,s),6.73(4H,s) [in DMSOd$_6$] |
| 159 | 3-OMe | 4-OMe | 5-OMe | 3 | 3 | Me | Me | 4-F | H | free base, pale yellow oil | 444 | 2230 (liq) | 1.67(3H,s),2.17(3H,s),3.84(3H,s),3.87(6H,s),3.95(2H,t,J=6.5Hz),6.62(2H,s), [in CDCl$_3$] |
| 160 | 3-OMe | 4-OMe | 5-OMe | 3 | 3 | Me | H | 2-OMe | H | oxalate | 442 | 2230 (KBr) | 1.75(3H,s),3.74,3.75(each 3H,s),3.85(6H,s),4.13(2H,t,J=5.5Hz),6.77(2H,s),6.93(4H,s) [in CD$_3$OD] |
| 161 | 3-OMe | 4-OMe | 5-OMe | 3 | 3 | Me | Me | 2-OMe | H | oxalate | 456 | 2230 (KBr) | 1.74(3H,s),2.89(3H,s),3.74,3.78(each 3H,s),3.84(6H,s),4.11(2H,t,J=5.5Hz),6.75(2H,s)6.94(4H,s) [in CD$_3$OD] |
| 162 | 3-OMe | 4-OMe | 5-OMe | 3 | 3 | Me | H | 3-OMe | H | oxalate | 442 | 2225 (KBr) | 1.75(3H,s),3.75(6H,s),3.86(6H,s),4.05(2H,t,J=6.0Hz),6.76(2H,s) [in CD$_3$OD] |
| 163 | 3-OMe | 4-OMe | 5-OMe | 3 | 3 | Me | Me | 3-OMe | H | free base, pale yellow oil | 456 | 2225 (liq) | 1.67(3H,s),2.17(3H,s),3.77(3H,s),3.84(3H,s),3.86(6H,s),3.98(2H,t,J=6.0Hz),6.62(2H,s) [in CDCl$_3$] |

TABLE 4-continued

| Example No. | R₁ | R₂ | R₃ | m | n | R₄ | R₅ | R₆ | R₇ | salt | Mass (M⁺) | IR cm⁻¹ (CN) | NMR δ ppm |
|---|---|---|---|---|---|---|---|---|---|---|---|---|---|
| 164 | 3-OMe | 4-OMe | 5-OMe | 3 | 3 | Et | H | 4-F | H | free base, pale yellow oil | 444 | 2230 (liq) | 0.93(3H,t,J=7.5Hz),2.69(2H,q,J=7.5Hz),3.85(3H,s),3.87(6H,s),3.96 (2H,t,J=6.0Hz),6.58(2H,s) [in CDCl₃] |
| 165 | 3-OMe | 4-OMe | 5-OMe | 3 | 3 | Et | Me | 4-F | H | free base, yellow oil | 458 | 2230 (liq) | 0.91(3H,t,J=7.5Hz),2.15(3H,s),3.85(9H,s),3.94(2H,t,J=6.5Hz),6.57 (2H,s) [in CDCl₃] |
| 166 | 3-OMe | 4-OMe | 5-OMe | 3 | 3 | Et | H | 2-OMe | H | free base, yellow oil | 456 | 2225 (liq) | 0.93(3H,t,J=7.0Hz),2.41(1H,s),3.80(3H,s),3.84(3H,s),3.86(6H,s), 4.07(2H,t,J=6.0Hz),6.59(2H,s),6.88(4H,s) [in CDCl₃] |
| 167 | 3-OMe | 4-OMe | 5-OMe | 3 | 3 | Et | Me | 2-OMe | H | free base, pale yellow oil | 470 | 2220 (liq) | 0.92(3H,t,J=7.0Hz),2.14(3H,s),3.84(3H,s),3.85(3H,s),3.86(6H,s), 4.04(2H,t,J=7.0Hz),6.58(2H,s),6.89(4H,s) [in CDCl₃] |
| 168 | 3-OMe | 4-OMe | 5-OMe | 3 | 3 | Et | H | 3-OMe | H | free base, fumarate | 456 | 2220 (KBr) | 0.92(3H,t,J=7.0Hz),3.75(6H,s),3.85(6H,s),3.84(3H,s),4.04(2H,t,J=6.0Hz),6.67 (2H,s),6.72(2H,s) [in CD₃OD] |
| 169 | 3-OMe | 4-OMe | 5-OMe | 3 | 3 | Et | Me | 3-OMe | H | free base, pale yellow oil | 470 | 2220 (KBr) | 0.91(3H,t,J=6.5Hz),2.15(3H,s),3.78(3H,s),3.84(3H,s),3.86(6H,s), 3.97(2H,t,J=6.0Hz),6.58(2H,s) [in CDCl₃] |
| 170 | 3-OMe | 4-OMe | 5-OMe | 3 | 3 | Et | H | 3-OMe | 5-OMe | fumarate | 486 | 2225 (KBr) | 0.92(3H,t,J=7.0Hz),3.72(6H,s),3.75(3H,s),3.85(6H,s),4.02(2H,t, J=6.0Hz),6.08(1H,s),6.67(2H,s),6.72(2H,s) [in CD₃OD] |
| 171 | 3-OMe | 4-OMe | 5-OMe | 3 | 3 | Et | Me | 3-OMe | 5-OMe | free base, pale yellow oil | 500 | 2225 (liq) | 0.91(3H,t,J=7.0Hz),2.14(3H,s),3.76(6H,s),3.84(3H,s),3.86(6H,s), 3.95(2H,t,J=6.0Hz),6.08(3H,s),6.58(2H,s) [in CDCl₃] |
| 172 | 3-OMe | 4-OMe | 5-OMe | 3 | 3 | nPr | H | 2-OMe | H | free base, pale yellow oil | 470 | 2225 (KBr) | 0.91(3H,t,J=7.0Hz),3.72,3.75(each 3H,s),3.84(6H,s),4.14(2H,t, J=5.5Hz),6.67(2H,s),6.73(2H,s),6.93(4H,s) [in CD₃OD] |
| 173 | 3-OMe | 4-OMe | 5-OMe | 3 | 3 | nPr | Me | 2-OMe | H | oxalate | 484 | 2225 (KBr) | 0.90(3H,t,J=6.5Hz),2.88(3H,s),3.75,3.78(each 3H,s),3.83(6H,s), 4.11(2H,m),6.72(2H,s),6.94(4H,s) [in CD₃OD] |
| 174 | 3-OMe | 4-OMe | 5-OMe | 3 | 3 | nPr | H | 3-OMe | H | fumarate | 470 | 2225 (KBr) | 0.90(3H,t,J=6.5Hz),3.72,3.75,3.85(each 6H,s),4.04(2H,t,J=5.5Hz),6.67 (2H,s),6.72(2H,s) [in CD₃OD] |
| 175 | 3-OMe | 4-OMe | 5-OMe | 3 | 3 | nPr | Me | 3-OMe | H | free base, pale yellow oil | 484 | 2225 (liq) | 0.87(3H,t,J=6.5Hz),2.14(3H,s),3.78,3.84(each 3H,s),3.86(6H,s), 3.97(2H,t,J=6.0Hz),6.57(2H,s) [in CDCl₃] |
| 176 | 3-OMe | 4-OMe | 5-OMe | 3 | 3 | nBu | H | 2-OMe | H | free base, pale yellow oil | 484 | 2225 (KBr) | 3.81,3.85(each 3H,s),3.86(6H,s),4.07(2H,t,J=6.0Hz),6.58(2H,s), 6.88(4H,s) [in CDCl₃] |
| 177 | 3-OMe | 4-OMe | 5-OMe | 3 | 3 | nBu | Me | 2-OMe | H | free base, pale yellow oil | 498 | 2225 (liq) | 2.14(3H,s),3.85,3.86(each 6H,s),4.04(2H,t,J=6.5Hz),6.58(2H,s), 6.89(4H,s) [in CDCl₃] |
| 178 | 3-OMe | 4-OMe | 5-OMe | 3 | 3 | nBu | H | 3-OMe | H | free base, fumarate | 484 | 2225 (KBr) | 0.87(3H,t,J=6.0Hz),3.78(3H,s),3.85(3H,s),3.87(6H,s),3.86(6H,s), J=6.0Hz),6.56(2H,s) [in CDCl₃] |
| 179 | 3-OMe | 4-OMe | 5-OMe | 3 | 3 | nBu | Me | 3-OMe | H | free base, yellow oil | 498 | 2230 (liq) | 0.86(3H,t,J=6.5Hz),2.14(3H,s),3.78(3H,s),3.85(3H,s),3.86(6H,s), 3.97(2H,t,J=6.0Hz),6.58(2H,s) [in CDCl₃] |
| 180 | 3-OMe | 4-OMe | 5-OMe | 3 | 3 | iBu | H | 2-OMe | H | fumarate | 484 | 2215 (KBr) | 0.72(3H,d,J=6.0Hz),1.01(3H,d,J=6.0Hz),3.73(3H,s),3.76(3H,S),3.85 (6H,s),4.13(3H,t,J=6.0Hz),6.67(2H,s),6.76(2H,s),6.93(4H,s) [in CD₃OD] |
| 181 | 3-OMe | 4-OMe | 5-OMe | 3 | 3 | iBu | Me | 2-OMe | H | free base, yellow oil | 498 | 2220 (liq) | 0.72(3H,d,J=6.0Hz),1.00(3H,d,J=6.0Hz),2.13(3H,s),3.85(6H,s),3.86 (6H,s),4.04(2H,d,J=6.0Hz),6.60(2H,s),6.89(4H,s) [in CDCl₃] |
| 182 | 3-OMe | 4-OMe | 5-OMe | 3 | 3 | iBu | H | 3-OMe | H | fumarate | 484 | 2220 (KBr) | 0.73(3H,d,J=6.0Hz),1.01(3H,d,J=6.0Hz),3.75(6H,s),3.86(6H,S),4.05 (2H,t,J=6.0Hz),6.67(2H,s),6.75(2H,s) [in CD₃OD] |
| 183 | 3-OMe | 4-OMe | 5-OMe | 3 | 3 | iBu | Me | 3-OMe | H | free base, yellow oil | 498 | 2220 (liq) | 0.71(3H,d,J=6.0Hz),0.99(3H,d,J=6.0Hz),2.14(3H,s),3.78(3H,s),3.85 (3H,s),3.86(6H,s),3.97(2H,t,J=6.0Hz),6.60(2H,s) [in CDCl₃] |
| 184 | 2-OMe | 3-OMe | 4-OMe | 3 | 3 | iPr | H | 2-OMe | H | oxalate | 470 | 2225 (KBr) | 0.80(3H,d,J=7.0Hz),1.15(3H,d,J=7.0Hz),3.72(3H,s),3.78(3H,s),3.84 (3H,s),3.91(3H,s),6.75(1H,s),6.93(4H,s),7.15(1H,d, J=9.0Hz) [in CD₃OD] |
| 185 | 2-OMe | 3-OMe | 4-OMe | 3 | 3 | iPr | Me | 2-OMe | H | free base, pale yellow oil | 484 | 2220 (liq) | 0.81(3H,d,J=7.0Hz),1.14(3H,d,J=7.0Hz),2.13(3H,s),3.81(3H,s),3.85 (6H,s),3.90(3H,s),3.86(6H,s),4.03(2H,t,J=7.0Hz),6.59(1H,d,J=9.0Hz),6.89(4H, s),7.14(1H,d,J=9.0Hz) [in CDCl₃] |

TABLE 5

| Example No. | salt | crystals | m.p. | (solvent) | Analysis for | (upper: calculated %, lower: found %) |
|---|---|---|---|---|---|---|
| 1 | hydrochloride | colorless prisms, | mp. 137~139° | (EtOH—iPr$_2$O) | C$_{25}$H$_{34}$N$_2$O$_4$·HCl | C, 64.85; H, 7.62; N, 6.05<br>C, 64.40; H, 7.71; N, 5.87 |
| 2 | hydrochloride | colorless needles, | mp. 111~112° | (iPrOH—iPr$_2$O) | C$_{24}$H$_{32}$N$_2$O$_4$·HCl | C, 64.20; H, 7.41; N, 6.24<br>C, 63.80; H, 7.80; N, 5.97 |
| 3 | hydrochloride | colorless needles, | mp. 175~176° | (EtOH—iPr$_2$O) | C$_{25}$H$_{34}$N$_2$O$_4$·HCl | C, 64.85; H, 7.62; N, 6.05<br>C, 64.47; H, 7.67; N, 5.86 |
| 4 | maleate | colorless needles, | mp. 130~132° | (EtOH—iPr$_2$O) | C$_{25}$H$_{34}$N$_2$O$_4$·C$_4$H$_4$O$_4$ | C, 64.19; H, 7.06; N, 5.16<br>C, 63.80; H, 7.19; N, 5.12 |
| 5 | hydrochloride | pale yellow prisms, | mp. 159~160° | (EtOH—iPr$_2$O) | C$_{25}$H$_{34}$N$_2$O$_3$·HCl | C, 67.17; H, 7.89; N, 6.27<br>C, 66.72; H, 8.20; N, 6.06 |
| 6 | hydrochloride | colorless scales, | mp. 155~158° | (EtOH—iPr$_2$O) | C$_{26}$H$_{36}$N$_2$O$_5$·HCl·½H$_2$O | C, 62.20; H, 7.43; N, 5.58<br>C, 62.38; H, 7.72; N, 5.39 |
| 10 | oxalate | colorless crystals, | mp. 155~156° | (EtOH—iPr$_2$O) | C$_{26}$H$_{35}$N$_3$O$_6$·½C$_2$H$_2$O$_4$ | C, 61.12; H, 6.84; N, 7.92<br>C, 60.80; H, 6.90; N, 7.83 |
| 11 | oxalate | colorless crystals, | mp. 118~120° | (EtOH—Et$_2$O) | C$_{26}$H$_{37}$N$_3$O$_4$·C$_2$H$_2$O$_4$·H$_2$O | C, 59.67; H, 7.33; N, 7.46<br>C, 59.39; H, 7.11; N, 7.16 |
| 14 | oxalate | colorless crystals, | mp. 108~110° | (CH$_3$CN—Et$_2$O) | C$_{27}$H$_{39}$N$_3$O$_4$·2C$_2$H$_2$O$_4$ | C, 57.31; H, 6.67; N, 6.47<br>C, 57.15; H, 6.87; N, 6.41 |
| 19 | hydrochloride | colorless needles, | mp. 128~129° | (EtOH—Et$_2$O) | C$_{24}$H$_{32}$N$_2$O$_3$·HCl | C, 66.58; H, 7.68; N, 6.47<br>C, 66.49; H, 7.64; N, 6.24 |
| 26 | oxalate | colorless needles, | mp. 128~129° | (EtOH) | C$_{26}$H$_{36}$N$_2$O$_3$·C$_2$H$_2$O$_4$ | C, 65.35; H, 7.44; N, 5.44<br>C, 65.33; H, 7.53; N, 5.31 |
| 31 | hydrochloride | colorless needles, | mp. 151~153° | (EtOH—iPr$_2$O) | C$_{24}$H$_{32}$N$_2$O$_3$·HCl·½H$_2$O | C, 65.22; H, 7.75; N, 6.34<br>C, 65.02; H, 7.73; N, 6.41 |
| 32 | oxalate | colorless crystals, | mp. 132~133° | (EtOH—iPr$_2$O) | C$_{25}$H$_{34}$N$_2$O$_3$·C$_2$H$_2$O$_4$ | C, 64.78; H, 7.25; N, 5.60<br>C, 64.16; H, 7.40; N, 5.30 |
| 33 | oxalate | colorless crystals, | mp. 172~174° | (EtOH—iPr$_2$O) | C$_{24}$H$_{31}$FN$_2$O$_3$·C$_2$H$_2$O$_4$ | C, 60.81; H, 6.67; N, 5.45<br>C, 60.66; H, 6.66; N, 5.23 |
| 34 | oxalate | colorless needles, | mp. 127~128° | (EtOH—iPr$_2$O) | C$_{25}$H$_{33}$FN$_2$O$_3$·C$_2$H$_2$O$_4$ | C, 62.54; H, 6.80; N, 5.40<br>C, 62.25; H, 7.15; N, 5.25 |
| 35 | hydrochloride | colorless needles, | mp. 147~149° | (EtOH—iPr$_2$O) | C$_{24}$H$_{31}$FN$_2$O$_3$·HCl·½H$_2$O | C, 62.66; H, 7.23; N, 6.09<br>C, 62.39; H, 7.42; N, 6.23 |
| 37 | oxalate | colorless needles, | mp. 158~162° | (EtOH) | C$_{24}$H$_{31}$FN$_2$O$_3$·C$_2$H$_2$O$_4$ | C, 61.89; H, 6.99; N, 5.55<br>C, 62.05; H, 6.99; N, 5.61 |
| 39 | hydrochloride | colorless plates, | mp. 147~148° | (EtOH—Et$_2$O) | C$_{24}$H$_{31}$ClN$_2$O$_3$·HCl | C, 61.67; H, 6.90; N, 5.99<br>C, 61.82; H, 7.02; N, 5.89 |
| 41 | hydrochloride | colorless needles, | mp. 185~186° | (EtOH) | C$_{24}$H$_{31}$ClN$_2$O$_3$·HCl | C, 61.67; H, 6.90; N, 5.99<br>C, 61.52; H, 7.08; N, 5.91 |
| 43 | hydrochloride | pale yellow needles, | mp. 132~135° | (EtOH—iPr$_2$O) | C$_{25}$H$_{34}$N$_2$O$_3$·HCl | C, 67.17; H, 7.89; N, 6.27<br>C, 66.76; H, 7.82; N, 6.13 |
| 45 | hydrochloride | colorless needles, | mp. 171~172° | (EtOH—iPr$_2$O) | C$_{25}$H$_{34}$N$_2$O$_3$·HCl | C, 67.17; H, 7.89; N, 6.27<br>C, 66.99; H, 7.98; N, 6.08 |
| 48 | hydrochloride | colorless prisms, | mp. 163~166° | (EtOH—iPr$_2$O) | C$_{25}$H$_{34}$N$_2$O$_4$·HCl | C, 64.85; H, 7.62; N, 6.05<br>C, 64.76; H, 7.83; N, 5.78 |
| 49 | hydrochloride | pale yellow needles, | mp. 171~173° | (EtOH—iPr$_2$O) | C$_{25}$H$_{31}$F$_3$N$_2$O$_3$·HCl | C, 59.84; H, 6.44; N, 5.59<br>C, 60.10; H, 6.69; N, 5.45 |
| 51 | hydrochloride | pale yellow needles, | mp. 173~175° | (EtOH—iPr$_2$O) | C$_{26}$H$_{36}$N$_2$O$_3$·HCl | C, 67.73; H, 8.09; N, 6.08<br>C, 67.59; H, 8.21; N, 5.91 |
| 52 | hydrochloride | pale yellow needles, | mp. 184~186° | (EtOH—iPr$_2$O) | C$_{25}$H$_{33}$ClN$_2$O$_3$·HCl | C, 62.37; H, 7.12; N, 5.82<br>C, 62.25; H, 7.27; N, 5.62 |
| 54 | oxalate | pale yellow crystals, | mp. 170~173° | (EtOH—iPr$_2$O) | C$_{26}$H$_{36}$N$_2$O$_5$·C$_2$H$_2$O$_4$·½H$_2$O | C, 60.53; H, 7.07; N, 5.04<br>C, 60.50; H, 7.36; N, 4.83 |

TABLE 5-continued

| Example No. | salt | crystals | m.p. | (solvent) | Analysis for | (upper: calculated %, lower: found %) |
|---|---|---|---|---|---|---|
| 55 | fumarate | colorless needles, | mp. 115~116° | (EtOH—Et$_2$O) | C$_{25}$H$_{33}$FN$_2$O$_3$.C$_4$H$_4$O$_4$ | C, 63.96; H, 6.85; N, 5.14<br>C, 63.83; H, 7.22; N, 5.07 |
| 61 | hydrochloride | colorless needles, | mp. 166~168° | (EtOH—iPr$_2$O) | C$_{25}$H$_{34}$N$_2$O$_4$.HCl.½H$_2$O | C, 63.61; H, 7.69; N, 5.83<br>C, 63.78; H, 7.90; N, 5.83 |
| 63 | oxalate | colorless needles, | mp. 147~148° | (EtOH—iPr$_2$O) | C$_{26}$H$_{36}$N$_2$O$_5$.C$_2$H$_2$O$_4$ | C, 61.53; H, 7.01; N, 5.12<br>C, 61.43; H, 7.22; N, 5.01 |
| 64 | hydrochloride | colorless prisms, | mp. 138~142° | (EtOH) | C$_{24}$H$_{32}$N$_2$O$_5$.HCl | C, 61.99; H, 7.15; N, 6.02<br>C, 61.82; H, 7.25; N, 5.92 |
| 66 | hydrochloride | colorless needles, | mp. 123~126° | (EtOH) | C$_{25}$H$_{34}$N$_2$O$_5$.HCl.½H$_2$O | C, 61.53; H, 7.43; N, 5.74<br>C, 61.61; H, 7.44; N, 5.58 |
| 67 | free base | colorless plates, | mp. 45~48° | (iPr$_2$O) | C$_{26}$H$_{36}$N$_2$O$_5$.H$_2$O | C, 65.80; H, 8.07; N, 5.90<br>C, 65.91; H, 8.28; N, 5.61 |
| 68 | hydrochloride | colorless needles, | mp. 163~166° | (EtOH) | C$_{26}$H$_{36}$N$_2$O$_5$.HCl | C, 63.34; H, 7.56; N, 5.68<br>C, 62.91; H, 7.75; N, 5.30 |
| 69 | free base | colorless prisms, | mp. 61~65° | (iPr$_2$O) | C$_{27}$H$_{38}$N$_2$O$_5$.H$_2$O | C, 66.37; H, 8.25; N, 5.73<br>C, 66.16; H, 8.46; N, 5.45 |
| 70 | hydrochloride | colorless plates, | mp. 176~179° | (MeOH) | C$_{27}$H$_{38}$N$_2$O$_5$.HCl | C, 63.96; H, 7.75; N, 5.52<br>C, 63.60; H, 7.92; N, 5.18 |
| 72 | hydrochloride | colorless needles, | mp. 185~188° | (MeOH) | C$_{27}$H$_{38}$N$_2$O$_5$.HCl | C, 63.96; H, 7.75; N, 5.52<br>C, 63.63; H, 7.99; N, 5.36 |
| 73 | free base | colorless prisms, | mp. 51~55° | (iPr$_2$O) | C$_{28}$H$_{40}$N$_2$O$_5$.H$_2$O | C, 66.91; H, 8.42; N, 5.57<br>C, 66.92; H, 8.67; N, 5.29 |
| 74 | hydrochloride | colorless needles, | mp. 135~136° | (EtOH—iPr$_2$O) | C$_{26}$H$_{36}$N$_2$O$_4$.HCl | C, 65.46; H, 7.82; N, 5.87<br>C, 65.19; H, 7.90; N, 5.79 |
| 79 | hydrochloride | colorless needles, | mp. 153~156° | (EtOH—iPr$_2$O) | C$_{26}$H$_{36}$N$_2$O$_4$.HCl.½H$_2$O | C, 64.25; H, 7.88; N, 5.76<br>C, 64.34; H, 7.74; N, 5.57 |
| 80 | oxalate | colorless needles, | mp. 137~138° | (EtOH) | C$_{27}$H$_{28}$N$_2$O$_4$.C$_2$H$_2$O$_4$ | C, 63.95; H, 7.40; N, 5.14<br>C, 63.88; H, 7.37; N, 5.00 |
| 81 | hydrochloride | pale yellow needles, | mp. 165~168° | (EtOH—iPr$_2$O) | C$_{26}$H$_{36}$N$_2$O$_4$.HCl | C, 65.46; H, 7.82; N, 5.87<br>C, 65.07; H, 8.15; N, 5.88 |
| 83 | hydrochloride | colorless needles, | mp. 102~105° | (EtOH—iPr$_2$O) | C$_{26}$H$_{36}$N$_2$O$_5$.HCl | C, 63.34; H, 7.56; N, 5.68<br>C, 62.98; H, 7.85; N, 7.51 |
| 84 | fumarate | colorless needles, | mp. 149~150° | (EtOH—iPr$_2$O) | C$_{26}$H$_{36}$N$_2$O$_5$.C$_4$H$_4$O$_4$ | C, 62.92; H, 7.04; N, 4.89<br>C, 62.62; H, 7.30; N, 4.76 |
| 85 | hydrochloride | colorless needles, | mp. 146~148° | (EtOH—iPr$_2$O) | C$_{27}$H$_{38}$N$_2$O$_5$.HCl | C, 63.96; H, 7.75; N, 5.52<br>C, 63.75; H, 8.01; N, 5.42 |
| 86 | hydrochloride | colorless plates, | mp. 186~189° | (EtOH) | C$_{27}$H$_{38}$N$_2$O$_6$.HCl | C, 62.00; H, 7.51; N, 5.36<br>C, 61.91; H, 7.47; N, 5.18 |
| 87 | hydrochloride | colorless plates, | mp. 167.5~170° | (EtOH) | C$_{27}$H$_{38}$N$_2$O$_5$.HCl | C, 63.96; H, 7.75; N, 5.52<br>C, 63.62; H, 7.78; N, 5.10 |
| 88 | fumarate | colorless needles, | mp. 118~119° | (EtOH) | C$_{24}$H$_{32}$N$_2$O$_5$.C$_4$H$_4$O$_4$ | C, 61.75; H, 6.66; N, 5.14<br>C, 61.54; H, 6.83; N, 5.06 |
| 89 | hydrochloride | colorless needles, | mp. 154~155° | (EtOH—Et$_2$O) | C$_{25}$H$_{34}$N$_2$O$_5$.HCl | C, 62.69; H, 7.36; N, 5.85<br>C, 62.31; H, 7.43; N, 5.73 |
| 91 | fumarate | colorless plates, | mp. 151~152° | (EtOH) | C$_{26}$H$_{36}$N$_2$O$_5$.C$_4$H$_4$O$_4$ | C, 62.92; H, 7.04; N, 4.89<br>C, 62.63; H, 7.38; N, 4.75 |
| 93 | fumarate | colorless crystals, | mp. 150~153° | (EtOH) | C$_{27}$H$_{38}$N$_2$O$_5$.C$_4$H$_4$O$_4$.½H$_2$O | C, 63.25; H, 7.13; N, 4.61<br>C, 63.33; H, 7.28; N, 4.66 |
| 94 | oxalate | colorless needles, | mp. 182~184° | (EtOH—Et$_2$O) | C$_{26}$H$_{36}$N$_2$O$_4$.C$_2$H$_2$O$_4$ | C, 63.38; H, 7.22; N, 5.28<br>C, 62.99; H, 7.34; N, 5.14 |
| 98 | fumarate | colorless crystals, | mp. 158.5~159.5° | (EtOH) | C$_{26}$H$_{35}$FN$_2$O$_4$.C$_4$H$_4$O$_4$ | C, 62.70; H, 6.84; N, 4.87<br>C, 62.47; H, 6.98; N, 4.82 |

TABLE 5-continued

| Example No. | salt | crystals | m.p. | (solvent) | Analysis for | (upper: calculated %, lower: found %) |
|---|---|---|---|---|---|---|
| 99 | oxalate | colorless crystals, | mp. 121.5~122.5° | (EtOH—iPr₂O) | C₂₇H₃₇FN₂O₄.C₂H₂O₄ | C, 61.91; H, 6.99; N, 4.98<br>C, 61.67; H, 7.10; N, 4.93 |
| 100 | fumarate | colorless needles, | mp. 147~148° | (EtOH—iPr₂O) | C₂₆H₃₅FN₂O₄.C₄H₄O₄ | C, 62.70; H, 6.84; N, 4.87<br>C, 62.80; H, 6.94; N, 4.87 |
| 101 | oxalate | colorless needles, | mp. 155~156° | (EtOH) | C₂₇H₃₇FN₂O₄.C₂H₂O₄ | C, 61.91; H, 6.99; N, 4.98<br>C, 61.94; H, 7.12; N, 5.00 |
| 104 | fumarate | colorless crystals, | mp. 160~161° | (EtOH—iPr₂O) | C₂₆H₃₅ClN₂O₄.C₄H₄O₄ | C, 60.96; H, 6.65; N, 4.74<br>C, 61.20; H, 6.78; N, 4.45 |
| 106 | fumarate | colorless needles, | mp. 123~125° | (EtOH—iPr₂O) | C₂₆H₃₅ClN₂O₄.C₄H₄O₄ | C, 60.96; H, 6.65; N, 4.74<br>C, 61.26; H, 6.80; N, 4.44 |
| 108 | oxalate | colorless needles, | mp. 135~136° | (EtOH—iPr₂O) | C₂₇H₃₈N₂O₄.C₂H₂O₄ | C, 63.95; H, 7.40; N, 5.14<br>C, 63.60; H, 7.61; N, 4.75 |
| 113 | oxalate | colorless needles, | mp. 132~133° | (EtOH) | C₂₈H₄₀N₂O₄.C₂H₂O₄ | C, 14.50; H, 7.58; N, 5.01<br>C, 14.48; H, 7.70; N, 4.99 |
| 114 | fumarate | colorless needles, | mp. 143~143.5° | (EtOH—iPr₂O) | C₂₇H₃₈N₂O₅.C₄H₄O₄ | C, 63.47; H, 7.22; N, 4.77<br>C, 63.48; H, 7.42; N, 4.73 |
| 115 | oxalate | colorless crystals, | mp. 132~133.5° | (EtOH—iPr₂O) | C₂₈H₄₀N₂O₅.C₂H₂O₄ | C, 62.70; H, 7.37; N, 4.87<br>C, 62.51; H, 7.40; N, 4.74 |
| 116 | oxalate | colorless crystals, | mp. 134~135° | (EtOH) | C₂₇H₃₈N₂O₅.C₂H₂O₄ | C, 62.13; H, 7.19; N, 5.00<br>C, 61.80; H, 7.26; N, 4.75 |
| 118 | fumarate | colorless plates, | mp. 112~113° | (EtOH—Et₂O) | C₂₇H₃₅N₂O₅.C₄H₄O₄ | C, 63.07; H, 7.22; N, 4.77<br>C, 63.07; H, 7.30; N, 4.70 |
| 120 | fumarate | colorless crystals, | mp. 151.5~152.5° | (EtOH—iPr₂O) | C₂₉H₄₂N₂O₄.C₄H₄O₄ | C, 66.20; H, 7.74; N, 4.68<br>C, 66.35; H, 7.82; N, 4.65 |
| 121 | oxalate | colorless crystals, | mp. 135~136° | (EtOH—Et₂O) | C₃₀H₄₄N₂O₄.C₂H₂O₄ | C, 65.51; H, 7.90; N, 4.77<br>C, 65.45; H, 8.01; N, 4.81 |
| 122 | fumarate | colorless needles, | mp. 151~152° | (EtOH) | C₂₉H₄₂N₂O₄.C₂H₂O₄ | C, 66.20; H, 7.74; N, 4.68<br>C, 66.19; H, 7.76; N, 4.68 |
| 126 | oxalate | colorless crystals, | mp. 177~180° | (DMF—EtOH) | C₂₆H₃₇N₃O₄.2C₂H₂O₄ | C, 56.69; H, 6.50; N, 6.61<br>C, 56.46; H, 6.47; N, 6.67 |
| 127 | oxalate | colorless crystals, | mp. 87~90° | (CH₃CN—Et₂O) | C₂₇H₃₉N₃O₄.2C₂H₂O₄.H₂O | C, 56.53; H, 6.73; N, 6.38<br>C, 56.69; H, 6.75; N, 6.10 |
| 128 | oxalate | pale yellow crystals, | mp. 132~134° | (DMF—iPr₂O) | C₂₆H₃₇N₃O₄.C₂H₂O₄.H₂O | C, 59.67; H, 7.33; N, 7.46<br>C, 59.68; H, 7.34; N, 7.31 |
| 129 | oxalate | colorless crystals, | mp. 94~97° | (CH₃CN—Et₂O) | C₂₇H₃₉N₃O₄.3/2C₂H₂O₄ | C, 59.60; H, 7.00; N, 6.95<br>C, 59.12; H, 6.98; N, 6.80 |
| 130 | fumarate | colorless crystals, | mp. 189~190° | (EtOH) | C₂₆H₃₅N₃O₆.C₄H₄O₄ | C, 59.89; H, 6.53; N, 6.98<br>C, 59.67; H, 6.70; N, 6.87 |
| 132 | fumarate | colorless crystals, | mp. 142~144° | (EtOH—iPr₂O) | C₂₆H₃₅N₃O₆.C₄H₄O₄ | C, 59.89; H, 6.53; N, 6.98<br>C, 59.83; H, 6.72; N, 6.94 |
| 134 | fumarate | colorless crystals, | mp. 148~149.5° | (EtOH—iPr₂O) | C₂₇H₃₈N₂O₅.C₄H₄O₄.½H₂O | C, 62.98; H, 7.25; N, 4.74<br>C, 62.92; H, 7.27; N, 4.66 |
| 136 | fumarate | colorless crystals, | mp. 145~148° | (EtOH—Et₂O) | C₂₇H₃₈N₂O₅.C₄H₄O₄ | C, 63.47; H, 7.22; N, 4.77<br>C, 63.26; H, 7.58; N, 4.57 |
| 137 | oxalate | colorless crystals, | mp. 155~158° | (EtOH—iPr₂O) | C₂₇H₃₈N₂O₅.C₂H₂O₄ | C, 63.13; H, 7.19; N, 5.00<br>C, 62.05; H, 7.46; N, 4.90 |
| 138 | fumarate | colorless crystals, | mp. 188~190° | (MeOH) | C₂₇H₃₅N₃O₄.C₄H₄O₄ | C, 64.01; H, 6.76; N, 7.22<br>C, 63.84; H, 6.88; N, 7.07 |
| 140 | fumarate | colorless crystals, | mp. 141~142.5° | (EtOH—iPr₂O) | C₃₃H₄₂N₂O₅.C₄H₄O₄ | C, 67.05; H, 7.00; N, 4.23<br>C, 66.59; H, 6.91; N, 4.04 |
| 141 | oxalate | colorless crystals, | mp. 125.5~126.5° | (EtOH—iPr₂O) | C₃₄H₄₄N₂O₅.C₂H₂O₄ | C, 66.44; H, 7.12; N, 4.30<br>C, 66.14; H, 7.25; N, 4.15 |

TABLE 5-continued

| Example No. | salt | crystals | m.p. | (solvent) | Analysis for | (upper: calculated %, lower: found %) |
|---|---|---|---|---|---|---|
| 142 | oxalate | colorless crystals, | mp. 116~120° | (EtOH—iPr$_2$O) | C$_{33}$H$_{42}$N$_2$O$_5$·C$_2$H$_2$O$_4$ | C, 66.02; H, 6.96; N, 4.40<br>C, 65.86; H, 6.94; N, 4.09 |
| 144 | fumarate | colorless needles, | mp. 156~157° | (EtOH—iPr$_2$O) | C$_{33}$H$_{42}$N$_2$O$_5$·C$_4$H$_4$O$_4$ | C, 67.05; H, 7.00; N, 4.23<br>C, 66.81; H, 7.04; N, 4.06 |
| 146 | hydrochloride | colorless needles, | mp. 129~130° | (EtOH—Et$_2$O) | C$_{28}$H$_{40}$N$_2$O$_6$·HCl·½H$_2$O | C, 61.58; H, 7.75; N, 5.13<br>C, 61.37; H, 7.64; N, 4.78 |
| 152 | fumarate | colorless crystals, | mp. 131.5~132° | (EtOH—Et$_2$O) | C$_{28}$H$_{40}$N$_2$O$_4$·C$_4$H$_4$O$_4$·½H$_2$O | C, 64.74; H, 7.64; N, 4.72<br>C, 64.98; H, 7.62; N, 4.49 |
| 158 | fumarate | colorless plates, | mp. 177~178° | (EtOH) | C$_{24}$H$_{31}$FN$_2$O$_4$·C$_4$H$_4$O$_4$ | C, 61.53; H, 6.45; N, 5.13<br>C, 61.37; H, 6.67; N, 5.10 |
| 160 | oxalate | colorless scales, | mp. 179~180° | (MeOH) | C$_{25}$H$_{34}$N$_2$O$_5$·C$_2$H$_2$O$_4$ | C, 60.89; H, 6.81; N, 5.26<br>C, 60.54; H, 6.93; N, 5.23 |
| 161 | oxalate | colorless needles, | mp. 137~138° | (EtOH) | C$_{25}$H$_{36}$N$_2$O$_5$·C$_2$H$_2$O$_4$ | C, 61.53; H, 7.01; N, 5.12<br>C, 61.07; H, 7.12; N, 5.03 |
| 162 | oxalate | colorless plates, | mp. 162~164° | (EtOH) | C$_{25}$H$_{34}$N$_2$O$_5$·C$_2$H$_2$O$_4$ | C, 60.89; H, 6.81; N, 5.26<br>C, 60.99; H, 7.06; N, 5.14 |
| 168 | fumarate | colorless plates, | mp. 110~112° | (EtOH—Et$_2$O) | C$_{26}$H$_{36}$N$_2$O$_5$·C$_4$H$_4$O$_4$ | C, 62.92; H, 7.04; N, 4.89<br>C, 63.03; H, 7.12; N, 4.82 |
| 170 | fumarate | colorless crystals, | mp. 111~114° | (EtOH—Et$_2$O) | C$_{27}$H$_{38}$N$_2$O$_6$·C$_4$H$_4$O$_4$ | C, 61.78; H, 7.02; N, 4.65<br>C, 61.46; H, 7.14; N, 4.41 |
| 172 | fumarate | colorless plates, | mp. 99~100° | (EtOH—Et$_2$O) | C$_{27}$H$_{38}$N$_2$O$_5$·C$_4$H$_4$O$_4$·½H$_2$O | C, 62.51; H, 7.28; N, 4.70<br>C, 62.28; H, 7.42; N, 4.55 |
| 173 | oxalate | colorless needles, | mp. 113~114° | (EtOH—Et$_2$O) | C$_{28}$H$_{40}$N$_2$O$_5$·C$_2$H$_2$O$_4$ | C, 62.70; H, 7.37; N, 4.87<br>C, 62.48; H, 7.41; N, 4.85 |
| 174 | fumarate | colorless plates, | mp. 129.5~130.5° | (EtOH) | C$_{27}$H$_{38}$N$_2$O$_5$·C$_4$H$_4$O$_4$ | C, 63.47; H, 7.22; N, 4.77<br>C, 63.09; H, 7.36; N, 4.69 |
| 180 | fumarate | colorless crystals, | mp. 106~108° | (EtOH—Et$_2$O) | C$_{28}$H$_{40}$N$_2$O$_5$·C$_4$H$_4$O$_4$·½H$_2$O | C, 63.04; H, 7.44; N, 4.59<br>C, 63.09; H, 7.45; N, 4.60 |
| 182 | fumarate | colorless needles, | mp. 133~135° | (EtOH) | C$_{28}$H$_{40}$N$_2$O$_5$·C$_4$H$_4$O$_4$ | C, 63.98; H, 7.38; N, 4.66<br>C, 63.89; H, 7.47; N, 4.51 |
| 184 | oxalate | colorless plates, | mp. 118~122° | (EtOH—iPr$_2$O) | C$_{27}$H$_{38}$N$_2$O$_5$·C$_2$H$_2$O$_4$·H$_2$O | C, 61.14; H, 7.08; N, 4.91<br>C, 60.86; H, 7.29; N, 5.00 |

We claim:

1. Alpha-aminoalkyl-alpha-alkylphenylacetonitrile derivatives represented by the general formula (I)

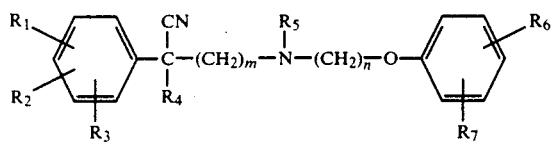

(I)

wherein $R_1$, $R_2$, and $R_3$, which may be the same or different, each represents hydrogen or lower alkoxy, $R_4$ represents a straight- or branched-chain lower alkyl, $R_5$ represents hydrogen or lower alkyl, $R_6$ and $R_7$, which may be the same or different, each represents hydrogen, halogen, lower alkyl, halogeno lower alkyl, lower alkoxy, nitro, amino, hydroxyalkyl, benzyloxy, cyano, or piperidinomethyl, and m and n are each an integer selected from 2 and 3, and pharmaceutically-acceptable acid addition salts thereof.

2. Compound of claim 1 being Alpha-isopropyl-alpha-[2-[N-[3-(2-methoxyphenoxy)propyl]amino]ethyl]-3,4,5-trimethoxyphenylacetonitrile.

3. Compound of claim 1 being, Alpha-isopropyl-alpha-[3-[N-[2-(3-methylphenoxy)ethyl]-N-methylamino]propyl]-3,4,5-trimethoxyphenylacetonitrile.

4. Compound of claim 1 being Alpha-isopropyl-alpha-[3-[N-[2-(2-methoxyphenoxy)ethyl]amino]propyl]-3,4,5-trimethoxyphenylacetonitrile.

5. Compound of claim 1 being Alpha-ethyl-alpha-[3-[N-[2-(2-methoxyphenoxy)ethyl]amino]propyl]-3,4,5-trimethoxyphenylacetonitrile.

6. Compound of claim 1 being Alpha-isobutyl-alpha-[3-[N-[2-(2-methoxyphenoxy)ethyl]amino]propyp]-3,4,5-trimethoxyphenylacetonitrile.

7. Compound of claim 1 being Alpha-isopropyl-alpha-[3-[N-[3-(3-methylphenoxy)propyl]-N-methylamino]propyl]-3,4,5-trimethoxyphenylacetonitrile.

8. Compound of claim 1 being Alpha-isopropyl-alpha-[3-[N-[3-(3-methoxyphenoxy)propyl]-N-methylamino]propyl]-3,4,5-trimethoxyphenylacetonitrile.

9. Compound of claim 1 being Alpha-isopropyl-alpha-[3-[N-[3-(2-methoxyphenoxy)propyl]amino]propyl]-3,4,5-trimethoxyphenylacetonitrile.

10. Compound of claim 1 being Alpha-ethyl-alpha-[3-[N-[3-(3-methoxyphenoxy)propyl]-N-methylamino]propyl]-3,4,5-trimethoxyphenylacetonitrile.

11. Compound of claim 1 being Alpha-propyl-alpha-[3-[N-[3-(3-methoxyphenoxy)propyl]-N-methylamino]propyl]-3,4,5-trimethoxyphenylacetonitrile.

12. A pharmaceutical composition useful in the treatment of cartino vaso diseases, peripheral circulatory insufficiency, and cerebral circulation failure, comprising one or more compounds as claimed in claim 1, or 2, or 3, or 4, or 11 in an amount effective for such purpose, together with compatible, pharmaceutically-acceptable carrier or coating.

13. A method for the treatment of a subject afflicted with cartino vaso disease, peripheral circulatory insufficiency, or cerebral circulation failure for alleviation of the same, comprising the step of administering to the said subject an amount of a compound of claim 1, or 2, or 3, or 4, or 11 effective for such purpose.

* * * * *